(12) United States Patent
Longley et al.

(10) Patent No.: US 11,998,470 B2
(45) Date of Patent: *Jun. 4, 2024

(54) REMOVABLE ORAL DEVICES FOR USE IN WEIGHT MANAGEMENT AND OTHER APPLICATIONS

(71) Applicant: SCIENTIFIC INTAKE LIMITED CO., Lawrence, MA (US)

(72) Inventors: William H Longley, Atlanta, GA (US); Richard P Schneider, Bedford, NY (US); Anthony R Tremaglio, Waban, MA (US); Marc M Gibeley, Boxford, MA (US)

(73) Assignee: SCIENTIFIC INTAKE LIMITED CO., Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/102,857

(22) Filed: Jan. 30, 2023

(65) Prior Publication Data

US 2023/0390092 A1 Dec. 7, 2023

Related U.S. Application Data

(63) Continuation of application No. 17/412,307, filed on Aug. 26, 2021, now Pat. No. 11,564,821, which is a continuation of application No. 15/702,549, filed on Sep. 12, 2017, now abandoned.

(Continued)

(51) Int. Cl.
*A61F 5/00* (2006.01)
*A61B 5/00* (2006.01)
(Continued)

(52) U.S. Cl.
CPC ............ *A61F 5/0006* (2013.01); *A61B 5/682* (2013.01); *A61B 13/00* (2013.01); *A61B 5/0017* (2013.01);
(Continued)

(58) Field of Classification Search
CPC ......... A61F 5/00–0006; A61F 5/56–58; A61B 5/0002; A61B 5/0015; A61B 5/0017;
(Continued)

(56) References Cited

U.S. PATENT DOCUMENTS 5,924,422 A * 7/1999 Gustafson ............. A61F 5/0006
128/846
7,182,596 B2 * 2/2007 Paulus ..................... A61C 7/10
433/21

FOREIGN PATENT DOCUMENTS

WO WO-2017006176 A1 * 1/2017 ........... A44C 15/007

* cited by examiner

*Primary Examiner* — Michelle J Lee
(74) *Attorney, Agent, or Firm* — Rhodes IP PLC; Christopher Rhodes

(57) ABSTRACT

Certain configurations of removable oral devices are described. In some instances, the removable oral device includes a palatal element. In certain configurations, the palatal element may comprise a variable hardness at different areas, e.g., edges can be softer than other areas of the removable oral device. In other instances, the removable oral device may comprise two or more individual palatal elements which together can form the palatal element and permit user adjustment of the oral volume. Various materials used in the palatal element are described. Sensors and other on-board devices are also described.

19 Claims, 8 Drawing Sheets

Related U.S. Application Data

(60) Provisional application No. 62/521,498, filed on Jun. 18, 2017, provisional application No. 62/477,752, filed on Mar. 28, 2017.

(51) Int. Cl.
| | | |
|---|---|---|
| *A61B 13/00* | (2006.01) | |
| *A61B 5/01* | (2006.01) | |
| *A61B 5/0537* | (2021.01) | |
| *A61B 5/08* | (2006.01) | |
| *A61B 5/083* | (2006.01) | |

(52) U.S. Cl.
CPC ............... *A61B 5/0088* (2013.01); *A61B 5/01* (2013.01); *A61B 5/0537* (2013.01); *A61B 5/082* (2013.01); *A61B 5/0833* (2013.01); *A61B 5/0836* (2013.01); *A61B 5/4836* (2013.01); *A61B 2503/10* (2013.01); *A61B 2562/0219* (2013.01); *A61B 2562/0247* (2013.01)

(58) Field of Classification Search
CPC ... A61B 5/0059; A61B 5/0077; A61B 5/0088; A61B 5/01; A61B 5/05; A61B 5/053; A61B 5/0537; A61B 5/08; A61B 5/082; A61B 5/083–0836; A61B 5/48; A61B 5/4836; A61B 5/68; A61B 5/6801; A61B 5/6802; A61B 5/6813; A61B 5/6814; A61B 5/682; A61B 2503/00; A61B 2503/10; A61B 2562/00; A61B 2562/02; A61B 2562/0219; A61B 2562/0247; A61B 13/00; A61B 1/00; A61B 1/24; A61C 7/00; A61C 7/08; A61C 7/10; A61C 7/36; A61C 19/06–08; A61C 13/0003–0006; A61C 13/0013; A61C 13/0002; A61C 7/002; A61C 9/00; A61C 9/004; A61C 9/0046; A63B 71/08–085; A63B 2071/086; A63B 2071/088; A61M 16/0488–0497; B33Y 40/20

See application file for complete search history.

REMOVABLE ORAL DEVICES FOR USE IN WEIGHT MANAGEMENT AND OTHER APPLICATIONS

PRIORITY APPLICATIONS

This application claims priority to and the benefit of U.S. 62/477,752 filed on Mar. 28, 2017 and entitled "REMOVABLE ORAL DEVICES" and claims priority to U.S. Provisional Application No. 62/521,498 filed on Jun. 18, 2017 and entitled "METHODS OF USING REMOVABLE ORAL DEVICES." The entire disclosure of each of these applications is hereby incorporated herein by reference for all purposes.

CROSS-REFERENCE TO RELATED APPLICATIONS

This application is related to, and incorporates by reference herein, each of the following patent applications: U.S. Provisional Application 62/477,760 filed on Mar. 28, 2017 and entitled "METHODS OF USING REMOVABLE ORAL DEVICES," U.S. Provisional Application 62/477,764 filed on Mar. 28, 2017 and entitled "METHODS OF PRODUCING REMOVABLE ORAL DEVICES," U.S. Provisional Application 62/477,766 filed on Mar. 28, 2017 and entitled "SYSTEMS INCLUDING REMOVABLE ORAL DEVICES," and U.S. Provisional Application 62/477,768 filed on Mar. 28, 2017 and entitled "REMOVABLE ORAL DEVICES AND THEIR USE IN COMBINATION WITH PHARMACOLOGICAL AGENTS, IMPLANTS AND OTHER DEVICES."

TECHNOLOGICAL FIELD

This application is directed to removable oral devices. More particularly, certain configurations described herein are directed to removable oral devices that can reduce the overall volume of the mouth to slow the intake of solid foods.

BACKGROUND

Many methods for controlling weight exist. Most existing methods do not provide long term weight loss or health benefits.

SUMMARY

Certain illustrative configurations are directed to removable oral devices which can be inserted into the mouth to reduce the overall food volume of the mouth. As noted in more detail below, the removable devices can be configured to reduce the overall usable volume of the mouth when solid food is received by the mouth and can be used, for example, to assist in weight loss and/or control weight gain. In other instances, the removable oral device may comprise one or more on-board sensors or other devices or components.

In some aspects, a removable oral device comprises a palatal element configured to contact a roof of a user's mouth at a palatal surface. For example, the palatal element comprises a body comprising a thickness configured to lower a vaulted area of the roof of the mouth to decrease an overall oral volume of the mouth to a first oral volume. In some instances, the body comprises a variable hardness across a tongue surface of the body, e.g., may comprise a softer edge or edges than material present at a central or apex area of the palatal element.

In certain examples, the removable oral device may also comprise a clasping element coupled to the palatal element. For example, the clasping element can be configured to assist in removal of the removable oral device when the removable oral device is inserted into the user's mouth.

In some instances, the tongue surface of the palatal element comprises a softer material at an edge of the palatal element and is substantially non-compressible at an area adjacent to the roof of the user's mouth. In other examples, the softer material at an edge of the palatal element has a decreased Vickers Hardness at body temperature compared to room temperature.

In certain examples, the palatal element comprises a temperature sensitive thermally expandable material configured to increase its overall volume at a body temperature of the user.

In some examples, the palatal element comprises one or more longitudinal grooves.

In other examples, the palatal element comprises an internal bladder.

In some configurations, the body of the palatal element is configured to reversibly couple to a second body, wherein the coupled body and second body provide a second oral volume less than the first oral volume. For example, the second body can be configured to reversibly couple to a third body, wherein the coupled body, second body and third body provide a third oral volume less than the second oral volume.

In certain embodiments, the body of the palatal element comprises a first material at the roof of the user's mouth and a second material adjacent to the clasp of the removable oral device, in which the second material is less hard than the first material to provide the variable hardness. In some instances, the first and second material may comprise a common polymer but may be crosslinked to a lesser degree in the second material.

In some examples, the removable oral device comprises a first clasping element and a second clasping element each coupled to the palatal element. For example, the first clasping element can be configured to engage a first respective molar surface of the user at one side of upper molars of the user, and the second clasping element can be configured to engage a second respective molar surface of the user at an opposite side of the upper molars. The clasping element can be configured to assist in removal of the removable oral device from the mouth and/or to retain the removable oral device in the user's mouth. In some instances, the first clasping element and the second clasping element do not engage any teeth other than the molar teeth of the user.

In certain examples, the palatal element and the clasping element (when present) do not alter a position of the user's teeth.

In other examples, the palatal element and the clasping element (when present) do not retain a position of the user's teeth.

In some embodiments, a Vickers Hardness of material at edges of the palatal element adjacent to teeth of the user, when the removable oral device is inserted into the user's mouth and is at a temperature substantially similar to mouth temperature of the user, is at least 20% less than a Vickers Hardness of material at an apex of the palatal element. For example, the Vickers Hardness of material at the apex of the palatal element can be at least 20 HV.

In other examples, the removable oral device can comprise a camera embedded in the palatal element.

In certain examples, the removable oral device can comprise an electrode positioned within the palatal element and comprising a surface configured to be exposed to fluid entering into the user's mouth.

In other embodiments, the removable oral device can comprise a bar code reader embedded in the palatal element.

In some examples, the removable oral device can comprise a processor embedded in the palatal element.

In additional embodiments, the removable oral device can comprise a memory unit electrically coupled to the processor.

In some instances, the removable oral device can comprise an optical transmitter embedded within the palatal element.

In further examples, the removable oral device can comprise a RFID tag embedded within the palatal element.

In some examples, the removable oral device can comprise a piezoelectric sensor embedded within the palatal element.

In other example, the removable oral device can comprise an accelerometer embedded within the palatal element.

In certain instances, the removable oral device can comprise a chewing sensor embedded within the palatal element.

In another aspect, a removable oral device comprises a palatal element, an optional clasping element and a processor. For example, the palatal element can be configured to contact a roof of a user's mouth at a palatal surface. The palatal element may comprise a body comprising a thickness configured to lower a vaulted area of the roof of the mouth to decrease an overall oral volume of the mouth to a first oral volume. If desired, the body may comprise a variable hardness across a tongue surface of the body, e.g., one or more edges may be softer than an apex area of the palatal element. When the clasping element is present, the clasping element can be coupled to the palatal element. For example, the clasping element can be configured to assist in removal of the removable oral device when the removable oral device is inserted into the user's mouth. The processor can be embedded within the palatal element so it is not generally exposed to food or fluids entering the mouth.

In some instances, the removable oral device can comprise a memory unit and an optical transmitter each embedded in the palatal element and each electrically coupled to the processor. For example, the optical transmitter can be configured to provide an optical signal to a case comprising an optical reader or an optical reader present in another device to transfer information from the removable oral device to the case (or other device). In other examples, the removable oral device can comprise a battery electrically coupled to each of the processor, the memory unit and the optical transmitter. In certain examples, a Vickers Hardness of material at edges of the palatal element adjacent to teeth of the user, when the removable oral device is inserted into the user's mouth and is at a temperature substantially similar to mouth temperature of the user, is at least 20% less than a Vickers Hardness of material at an apex of the palatal element.

In an additional aspect, a removable oral device comprises a palatal element coupled to a clasping element. In certain configurations, the palatal element can be configured to contact a roof of a user's mouth at a palatal surface and comprises a body comprising a thickness configured to lower a vaulted area of the roof of the mouth to decrease an overall oral volume of the mouth to a first oral volume. If desired, the body comprises a variable hardness across a tongue surface of the body. In certain examples, the clasping element, when present, can be configured to assist in removal of the removable oral device from the user's mouth.

In another aspect, a removable oral device comprises a palatal element coupled to a clasping element and a camera. In certain configurations, the palatal element can be configured to contact a roof of a user's mouth at a palatal surface and comprises a body comprising a thickness configured to lower a vaulted area of the roof of the mouth to decrease an overall oral volume of the mouth to a first oral volume. The clasping element, when present, can be configured to assist in removal of the removable oral device from the user's mouth The camera can be within the body of the palatal element. For example, the camera can be configured to capture images of material placed in the mouth of the user.

In an additional aspect, a removable oral device comprises a palatal element coupled to a clasping element and at least one electrode. In certain configurations, the palatal element can be configured to contact a roof of a user's mouth at a palatal surface and comprises a body comprising a thickness configured to lower a vaulted area of the roof of the mouth to decrease an overall oral volume of the mouth to a first oral volume. The clasping element, when present, can be configured to assist in removal of the removable oral device from the user's mouth. The at least one electrode can be positioned within the body and exposed to fluid entering and exiting the mouth of the user. For example, the at least one electrode can be configured to measure athletic performance from the fluid entering and exiting the mouth of the user.

In an additional aspect, a removable oral device comprises a palatal element coupled to a clasping element and a bar code reader. In certain configurations, the palatal element can be configured to contact a roof of a user's mouth at a palatal surface and comprises a body comprising a thickness configured to lower a vaulted area of the roof of the mouth to decrease an overall oral volume of the mouth to a first oral volume. The clasping element, when present, can be configured to assist in removal of the removable oral device from the user's mouth. In some examples, a bar code reader can be within the body of the palatal element. In certain instances, the bar code reader is configured to read a bar code present on a material placed in the mouth of the user.

In another aspect, a removable oral device comprises a palatal element coupled to a clasping element and a processor. In certain configurations, the palatal element can be configured to contact a roof of a user's mouth at a palatal surface and comprises a body comprising a thickness configured to lower a vaulted area of the roof of the mouth to decrease an overall oral volume of the mouth to a first oral volume. The clasping element, when present, can be configured to assist in removal of the removable oral device from the user's mouth. In certain configurations, a processor and an optional memory unit may be within the body of the palatal element. If desired, the memory unit may comprise desired information such as a nutrition plan or an updatable electronic medical record of the user.

In another aspect, a removable oral device comprises a palatal element coupled to a clasping element and a piezoelectric sensor. In certain configurations, the palatal element can be configured to contact a roof of a user's mouth at a palatal surface and comprises a body comprising a thickness configured to lower a vaulted area of the roof of the mouth to decrease an overall oral volume of the mouth to a first oral volume. The clasping element, when present, can be configured to assist in removal of the removable oral device from the user's mouth. In certain configurations, a piezoelectric sensor within the body of the palatal element can be present. For example, the piezoelectric sensor can be configured to measure movement of the upper jaw during chewing.

In an additional aspect, a removable oral device comprises a palatal element coupled to a clasping element and an accelerometer. In certain configurations, the palatal element can be configured to contact a roof of a user's mouth at a palatal surface and comprises a body comprising a thickness configured to lower a vaulted area of the roof of the mouth to decrease an overall oral volume of the mouth to a first oral volume. The clasping element, when present, can be configured to assist in removal of the removable oral device from the user's mouth. In some examples, the accelerometer can be within the body of the palatal element. The accelerometer can be used for many different uses, e.g., the accelerometer can be configured to measure impact force.

In an additional aspect, a removable oral device comprises a palatal element coupled to a clasping element and an electrode. In certain configurations, the palatal element can be configured to contact a roof of a user's mouth at a palatal surface and comprises a body comprising a thickness configured to lower a vaulted area of the roof of the mouth to decrease an overall oral volume of the mouth to a first oral volume. The clasping element, when present, can be configured to assist in removal of the removable oral device from the user's mouth. In some examples, the electrode can be positioned within the body of the palatal element and may be configured, for example, to measure bioelectrical impedance to determine a body fat percentage of the user.

In another aspect, a removable oral device comprising a palatal element and a clasping element is provided. In some examples, the palatal element is configured to contact a roof of a user's mouth at a palatal surface and comprises a body comprising a thickness configured to lower a vaulted area of the roof of the mouth to decrease an overall oral volume of the mouth to a first oral volume. The clasping element, when present, can be configured to assist in removal of the removable oral device from the user's mouth. In some configurations, the clasping element does not include any supporting wires or other structures.

In an additional aspect, a removable oral device comprising a palatal element coupled to a clasping element where the clasping element comprises a continuous wire structure terminating in the body of the palatal element, and wherein the continuous wire structure has a smaller outer wire diameter at termini of the wire structure within the clasping element than an outer wire diameter within the palatal element is described. If desired, a clasping element can be coupled to each side of the palatal element. The clasping element(s), when present, can be configured to assist in removal of the removable oral device from the user's mouth.

In another aspect, a removable oral device comprises a palatal element coupled to a clasping element. The palatal element can be configured to contact a roof of a user's mouth at a palatal surface. The palatal element comprises a body comprising a thickness configured to lower a vaulted area of the roof of the mouth to decrease an overall oral volume of the mouth to a first oral volume. The palatal element comprises a lower thickness at a front section adjacent to inner surfaces of the anterior teeth to reduce lisping compared to a thickness at an apex section of the palatal element. The clasping element, when present, can be configured to assist in removal of the removable oral device from the user's mouth.

In an additional aspect, a removable oral device comprises a palatal element coupled to a clasping element, wherein the palatal element comprises a thermally expandable material configured to increase its volume with increasing temperature to decrease the overall oral volume to a second oral volume less than the first oral volume. The clasping element, when present, can be configured to assist in removal of the removable oral device from the user's mouth.

In another aspect, a removable oral device may comprise a first palatal element and a second palatal element. The first palatal element can be configured to contact a roof of a user's mouth at a palatal surface and comprises a body comprising a thickness configured to lower a vaulted area of the roof of the mouth to decrease an overall oral volume of the mouth to a first oral volume. The first palatal element can be configured to reversibly couple to the second palatal element to decrease the overall oral volume of the mouth to a second oral volume less than the first oral volume.

In an additional aspect, a removable oral device comprises a palatal element coupled to a clasping element and a chewing sensor. In certain configurations, the palatal element can be configured to contact a roof of a user's mouth at a palatal surface and comprises a body comprising a thickness configured to lower a vaulted area of the roof of the mouth to decrease an overall oral volume of the mouth to a first oral volume. The clasping element, when present, can be configured to assist in removal of the removable oral device from the user's mouth. The chewing sensor can be configured to provide sensory feedback to the user between swallowing of food in the user's mouth.

In another aspect, a kit comprises a first removable oral device and a second removable oral device. The first removable oral device comprises a palatal element coupled to a clasping element. The palatal element of the first removable oral device can be configured to contact a roof of a user's mouth at a palatal surface. The palatal element of the first removable oral device comprises a body comprising a thickness configured to lower a vaulted area of the roof of the mouth to decrease an overall oral volume of the mouth to a first oral volume. The clasping element of the first removable oral device, when present, can be configured to assist in removal of the removable oral device from the user's mouth. The second removable oral device comprises a palatal element coupled to a clasping element. The palatal element of the second removable oral device configured to contact a roof of a user's mouth at a palatal surface and comprises a body comprising a thickness configured to lower a vaulted area of the roof of the mouth to decrease an overall oral volume of the mouth to a second oral volume less than the first oral volume. The clasping element of the second removable oral device, when present, can be configured to assist in removal of the removable oral device from the user's mouth.

In an additional aspect, a kit comprises a first palatal element, a second palatal element and a clasping element configured to couple to one of the first palatal element and the second palatal element. The first palatal element is configured to contact a roof of a user's mouth at a palatal surface and comprises a body comprising a thickness configured to lower a vaulted area of the roof of the mouth to decrease an overall oral volume of the mouth to a first oral volume. The second palatal element is configured to contact a roof of a user's mouth at a palatal surface, and comprises a body comprising a thickness configured to lower a vaulted area of the roof of the mouth to decrease an overall oral volume of the mouth to a second oral volume less than the first oral volume.

In another aspect, a kit comprises, a first palatal element coupled to a clasping element and a second palatal element configured to reversibly couple to the first palatal element.

The first palatal element can be configured to contact a roof of a user's mouth at a palatal surface and comprises a body comprising a thickness configured to lower a vaulted area of the roof of the mouth to decrease an overall oral volume of the mouth to a first oral volume. The clasping element is configured to retain the palatal surface of the first palatal element against the roof of the user's mouth when the removable oral device is inserted into the user's mouth. The second palatal element is configured to reversibly couple to the first palatal element to provide a second oral volume less than the first oral volume when the first and second palatal elements are coupled to each other.

Additional aspects, examples, embodiments and configurations are described further below.

BRIEF DESCRIPTION OF THE SEVERAL VIEWS OF THE DRAWINGS

Certain configurations of removable oral devices are described below with reference to the accompanying figures in which.

It will be recognized by the person of ordinary skill in the art, given the benefit of this disclosure, that the palatal elements, clasping elements, processors, sensors, etc. are not necessarily shown to scale.

DETAILED DESCRIPTION

Various components are described below in connection with illustrative configurations or removable oral devices. The exact configuration of the removable oral device may depend, at least in part, on the intended use of the removable oral device. As noted below, the removable oral device can be configured to insert into a user's mouth and can be removed by the user from their mouth without the use of any separate fasteners, insertion tools or other separate components or devices.

In certain configurations, the removable oral devices described herein are not intended to alter or retain the teeth in any particular position, e.g., the removable oral devices do not function as, or in the same way, as an orthodontic retainer. For example, in use a typical user only inserts the removable oral device during their meals, snacks, etc., which is typically a period less than 1 hour or even less than 30 minutes.

In certain examples, a removable oral device may generally comprise a palatal element optionally coupled to one or more clasping elements. The palatal element generally comprises a suitable shape and materials to place an upper surface of the palatal element in contact with a roof of a user's mouth. The clasping element, when present, can be configured to assist in removal of the removable oral device from the user's mouth. In other configurations, the clasping element, when present, can be configured to engage some surfaces of the user's upper teeth, e.g., inner surface and outer surfaces, to assist in retention of palatal element in place when the removable oral device is inserted into the user's mouth.

Figure 1:
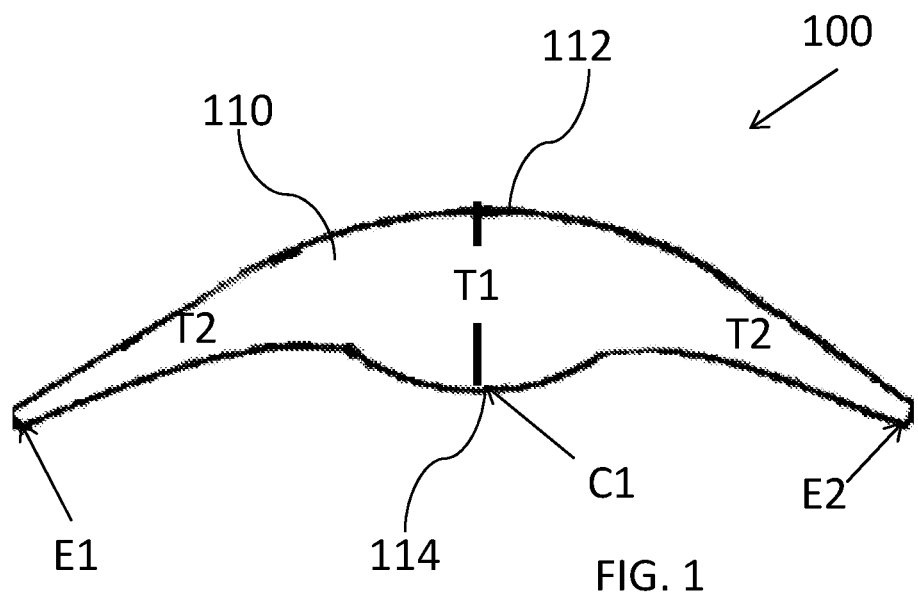
FIG. 1 is a side view of a palatal element of a removable oral device, in accordance with certain examples.

In certain examples, FIG. 1 shows a generalized illustration of one configuration of a palatal element of a removable oral device. The palatal element 100 comprises a body 110 comprising a palatal surface 112 and a tongue surface 114. As noted in more detail in U.S. 62/477,764 referenced above, the palatal element 100 can be produced using molding, printing or other suitable techniques. Notwithstanding that many different methods and devices can be used to produce the palatal element 100, the palatal element 100 is generally designed so the palatal surface 112 conforms or contours to the roof of a user's mouth. A tongue surface 114 generally mirrors or replicates the roof or palate shape of the user. In some instances, the palatal element 100 has a thickness T1 (from the highest point or apex of the palatal surface 112 to the lowest point of the tongue surface 114) at a medial portion of the palatal element 100. The thickness T2 at an edge of the palatal element 100 is generally less than the thickness T1. For example, the portions of the palatal element 100 which sit against or are adjacent to the upper teeth are typically 2×, 3×, 4× or 5× less thick than the thickness T1 to provide a more comfortable fit in a user's mouth. As noted in more detail herein, the thickness T1 may be adjusted or adjustable as desired. Without wishing to be bound by any particular theory or configuration, the thickness T1 can be selected to decrease the overall oral volume of the mouth available for chewing and/or to better position one or more sensors of the palatal element 100 in an appropriate position. The amount by which the oral volume is reduced is controlled generally by the thickness T1 and may vary from user to user or depending on the particular disorder to be treated, the particular condition to be monitored, feedback received by application software from a coach and other criteria. While the exact reduction in volume can vary, in some examples, the thickness T1 is selected such that the oral volume is reduced by 5% to about 50% (as compared to an original oral volume where no removable oral device is present), more particularly reduced by about 15% to about 35% or about 25% to about 35%. As noted in more detail below, the thickness of the palatal element may be altered with increasing temperature, by coupling one or more additional palatal element bodies to the palatal element or by other means. For example, an expandable bladder, e.g., an air bladder or liquid bladder, can be present in the palatal element 100 to alter the overall volume of the palatal element 100.

In certain embodiments, the removable oral device comprising the palatal element 100 can be used to reduce the overall volume of the mouth to slow food intake. For example, the decrease in overall volume provided when the palatal element 100 is inserted into a user's mouth 100 permits smaller bites of food and/or lower overall food volume per bite to be introduced into the mouth, which can enhance mindful eating practices. This result can increase the overall time it takes to ingest a particular volume of food, which can promote increased satiety and an overall reduction in food intake volume, e.g., fewer overall calories are consumed when the removable oral device is present compared to the removable oral device not being inserted into a user's mouth.

In some instances, the removable oral device comprising the palatal element, e.g., one without a clasping element or one with a clasping element, can be used in weight management and/or weight control. For example, a user can insert the removable oral device prior to eating, e.g., once per day, twice per day, three times per day, once per week, five days per week, twice per week, every time a user ingests food, etc. to assist in weight management. As noted herein, when the removable oral device is in place, the overall level of calories ingested during a particular eating session can be reduced, which can result in weight loss and/or weight management. In addition, by forcing the user to chew a particular quantity of food for a longer period, mindful eating practices can be adopted through behavioral modification. In certain configurations, and as described in more detail in commonly assigned applications bearing application numbers U.S. 62/477,760 and U.S. 62/477,766, the removable oral device can be used in combination with a coaching platform or coaching based devices to provide feedback and/or monitoring of the user's use of the removable oral device and/or to assist in weight management. Such coaching platforms may take the form of in-person sessions, external sessions over a remote connection or automated sessions retrieved by the user through one or more software applications on a mobile device or other electronic device.

In some instances, the removable oral device comprising a palatal element can be used until a user's body fat percentage or body mass index (BMI) reaches a desired level. For example, the removable oral device can be used in weight management with people having a body mass index between 25 and 30. If desired, the removable oral device could also be used with people whose body mass index exceeds 30 or is under 25. In some examples, the removable oral device can be used with human males comprising a body fat percentage between 22-29% or exceeding 26% or with human females comprising a body fat percentage of 31-39% or exceeding 31%. In some examples, the removable oral device frequency can be reduced once the user's BMI or body fat percentage drops below a selected level, e.g., below a BMI of 25 or below a body fat percentage of 22% or 25% for human males and 31% for human females. For example, weight maintenance can be attained by using the removable oral device once per week or 2-3× per week rather than using the removable oral device daily to assist in weight loss.

Figure 2:
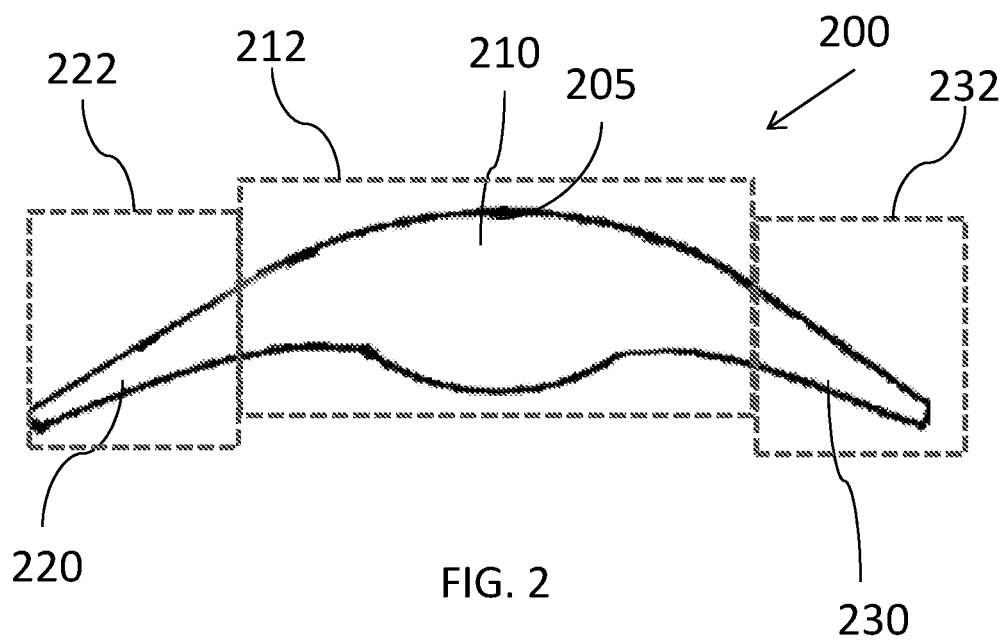
FIG. 2 is another side view of a palatal element of a removable oral device, in accordance with certain examples.

In certain examples and referring to FIG. 2, a palatal element 200 is shown that comprises areas 210, 220 and 230. Area 210 is designed to provide a desired thickness to reduce the overall oral volume and comprises an apex 205, which is typically the highest point of the palatal element 200. Areas 220 and 230 are designed to be positioned adjacent to certain teeth and assist in retention of the removable oral device in place. In certain configurations, the material present in area 210 (as shown by box 212) may be harder than the materials present in areas 220, 230 (as shown by boxes 222 and 232). The softness of the materials at areas 220, 230 can be the same or can be different. In some examples, areas 220, 230 comprise softer materials to permit these areas to function, at least to some degree, as a seal or gasket that prevent foods or other materials from entering into any space between a palatal surface of the palatal element and the roof of the user's mouth. Depending on the particular materials used, the hardness at the areas 220, 230 is at least 2×, 3×, 4× or 5× less than the hardness at area 210. The hardness at area 210 is generally less than that of glass or hard plastics such that the area 210 can flex to some degree during chewing of food.

Referring again to FIG. 1, the hardness of the materials may decrease from a central area C1 toward the edges E1, E2. In some examples, hardness may gradually decrease from C1 to E1, E2, whereas in other instances an interface can be present between various portions of the palatal element where the softer materials meet the harder materials. In some embodiments and referring again to FIG. 2, the material present in area 210 (as shown by box 212) may be harder, e.g., may have a higher Vickers hardness value (HV), than the materials present in at least some areas within areas 220, 230 (as shown by boxes 222 and 232). While the exact methodology used to determine a HV value can vary, suitable methods typically involve indenting the test material with a diamond indenter under a selected load, e.g., 30 kg of force (kgf), and measuring the depth of the indentation. The indentation depth can be correlated to materials hardness using suitable lookup tables or calibration curves. Commercial instruments to determine Vickers hardness values are available from Shimadzu (Japan) and LECO (Japan). In some instances, the protocols described in ASTM E384-16 entitled "Standard Test Method for Microindentation Hardness of Materials" can be followed to determine Vickers hardness values. The hardness/softness of the materials at areas 220, 230 can be the same or can be different. In some examples, areas 220, 230 comprise softer materials (compared to the hardness of the material at area 210) to permit these areas to function, at least to some degree, as a seal or gasket that prevent foods or other materials from entering into any space between a palatal surface of the palatal element and the roof of the user's mouth. Depending on the particular materials used, the hardness at the areas 220, 230 can be at least 2×, 3×, 4× or 5× less than the hardness at area 310. For example, the Vickers hardness value (HV) at areas 220, 230 can be at least 5% less, at least 10% less, at least 20% less, at least 30% less, at least 40% less or at least 50% less than the HV at the area 210. The hardness at area 210 is generally less than that of glass or hard plastics such that the area 210 can flex to some degree during chewing of food.

For example, in some instances, the HV at the apex 205 may be 20 HV or more, whereas the HV at each of the edges 220, 230 can independently be less than 20 HV. In other examples, the HV at the apex 205 can be 10 HV or more and the value at the edges 220, 230 can be less than 10 HV. In other configurations, the HV value at the apex 205 can be 10 HV or more and the value at the edges 220, 230 can be less than or equal to 5 HV. The exact level of hardness used may vary from subject to subject. For example, certain individuals may find hard apex areas to be uncomfortable, and the material hardness at the apex can be lowered for those subjects by, for example, reducing the level of cross-linking in the polymeric materials used to produce the palatal element 200.

In some embodiments, the material used at the edges may be the same or may be different than material present at the apex of the palatal element. For example, the material at the edges can be the same material but it may be cross-linked to a lesser degree to be softer than the material at the apex section of the palatal element. In other examples, a different material is used for the edges and is coupled to other material of the palatal element through one or more cross-linkers. Where two different materials are used, there is generally no discernible interface between the materials which might be obtrusive or uncomfortable. In some instances, the material of the apex portion can be built up using "sprinkle and pour" methods until a desired thickness is reached. For example, layers of the apex material can be built up using a first material, and a second material can then be coupled to the first material to provide the edges of the palatal element.

In some embodiments, the material present in the palatal element may be an acrylic, a polycarbonate, a polyolefin, a thermoplastic polymer, a thermoset polymer or combinations thereof. If desired, the material may comprise elastomers, elastomeric fibers or other materials to alter the overall hardness of one or more areas of the palatal element. The materials can be cross-linked or cured by sprinkling or mixing a cross-linker with the material either pre-use or post-use. For example, a mold of the user's mouth can be used with the material to provide a palatal element. The material can be added to the mold (in one or more desired areas) and then cross-linked by sprinkling a cross-linker onto the added material in the mold. Other methods and processes for producing the palatal element are described in more detail in the commonly assigned Application No. U.S. 62/477,764 incorporated herein by reference. In some examples, the palatal surface and/or tongue surface can be smooth to prevent food from sticking to the removable oral device. If desired, however, the surface may be bumpy or comprise ridges or other features to mimic the tongue feel when the tongue is placed against the roof of the user's mouth. In other instances, the palatal element may comprise one or more coatings including, but not limited to, anti-bacterial coatings, non-stick coatings or coatings which may impart color or ornamental designs to the palatal element. In some embodiments, each area of the palatal element may comprise an acrylic material including polyacrylates, methacrylates and the like. In some embodiments, one or more areas of the palatal element may comprise Silident materials, clays, alginates, or other materials which can generally retain their shape during eating forces. In some examples, the palatal element may comprise one or more photo-curable, heat curable, UV curable or cured materials. The exact materials used may include, but are not limited to, acrylates, methacrylates, acrylic polymers and co-polymers, functionalized bisphenol A methacrylates such as a mono-functional bisphenol A dimethacrylate or a difunctional bisphenol A dimethacrylate, a diglycidyl methacrylate ester of bisphenol-A or a bisphenol-A diglycidyl ether and other materials. In some examples, the palatal element of the removable oral device may comprise one or more of ethylene glycol dimethacrylate, diethylene glycol dimethacrylate, triethylene glycol dimethacrylate, polyethylene glycol dimethacrylate, 2,2 bis[4-(methacryloxy ethoxy)phenyl]propane, tricyclodecane dimethanol dimethacrylate, 1,10-decanediol dimethacrylate, 1,6-hexanediol dimethacrylate, 1,9-nonanediol dimethacrylate, neopentyl glycol dimethacrylate, 2-hydroxy 1-3 dimethacryloxy propane, trimethylolpropane trimethacrylate, ethoxylated trimethylol propane trimethacrylate, ditrimethyolpropane tetramethacrylate, tris (2-hydroxy ethyl)isocyanurate trimethacrylate, dipentaerythritol pentamethacrylate, ethoxylated pentaerythritol tetramethacrylate, propoxylated glyceryl trimethacrylate, propoxylated trimethylolpropane trimethacrylate, and a polyester dendrimer. The exact material used, or combinations of the materials used, can be selected to provide a palatal element which provides sufficient hardness to permit chewing but is not so hard as to be uncomfortable in the mouth. For example, the material can be cured to provide a feel similar to the native roof of the mouth.

In some examples, the material at the edges of the palatal element may be thermally sensitive and can soften to an even greater degree at mouth temperatures than when the palatal element is outside of the mouth. For example, the Vickers hardness of the material at the edges can be selected to decrease when the removable oral device is inserted into the mouth and reaches the temperature of the mouth compared to the Vickers hardness of the edges when the palatal element is at room temperature. In some embodiments, the Vickers hardness of the material of the edges decreases at least 5%, at least 10% or at least 20% at about 37 degrees Celsius compared to the Vickers hardness at room temperature (about 25 degrees Celsius).

Figure 3:
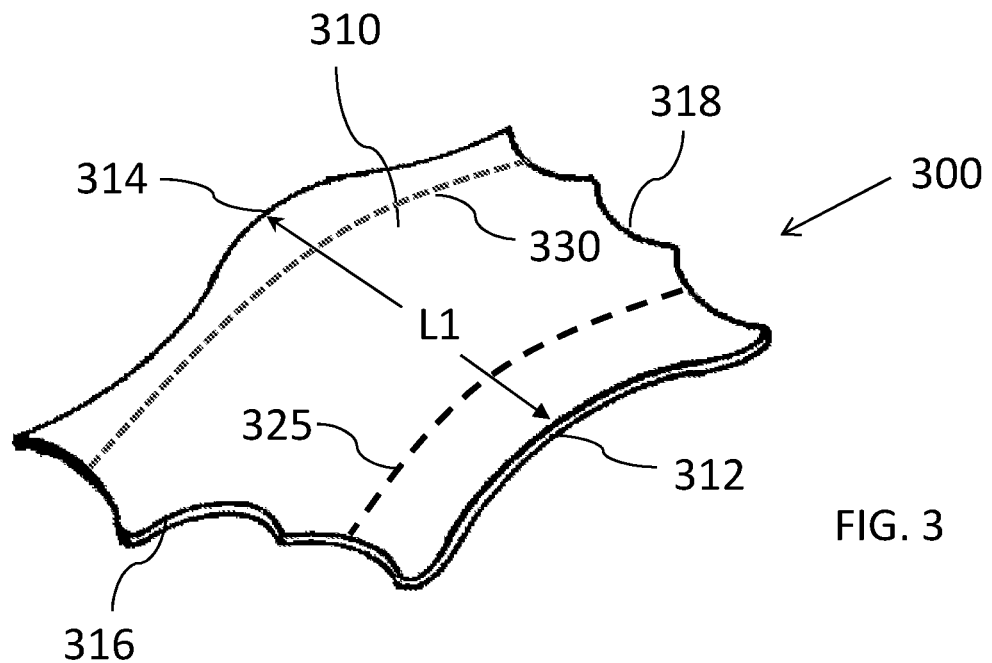
FIG. 3 is a perspective view of a palatal element of a removable oral device, in accordance with certain configurations.

In certain examples, a perspective view of a palatal element is shown in FIG. 3. The palatal element 300 comprises a body 310 with sides 312, 314, 316 and 318. Side 312, e.g., an anterior side, generally is adjacent and/or contact inner surfaces of the anterior teeth. Side 314, e.g., a posterior side, is positioned in the back of the mouth when the removable oral device is inserted. Side 316 can be positioned adjacent to the inner surfaces of tooth numbers 1-4 (or 2-4 when the wisdom teeth have been removed) when the removable oral device is inserted. Side 318 can be positioned adjacent to the inner surfaces of tooth numbers 13-16 (or 13-15 when the wisdom teeth have been removed) when the removable oral device is inserted. The length L1 of the body 310 may vary and is generally designed to be large enough so the body 310 provides a desired oral volume reduction but is not so large that a user may gag or have difficulty breathing when the removable oral device is inserted. As noted herein, the sides 316, 318 may comprise a softer material than material present at an apex of the palatal element 300, e.g., the Vickers hardness at the edges 316, 318 may be at least 2×, 3×, 4× or 5× less than the hardness at an apex area. For example, the Vickers hardness value (HV) at the edges 316, 318 can be at least 5% less, at least 10% less, at least 20% less, at least 30% less, at least 40% less or at least 50% less than the HV value at the apex area of the palatal element 300.

In some examples, some portion or the anterior side and/or posterior side can be removed to facilitate a better user experience with the removable oral device. For example, a volume of the palatal element toward the anterior side 312, e.g., the volume from the line 325 forward toward the anterior side 312 can be removed or reduced to reduce lisping. In certain embodiments, about 1-10% of the volume from the anterior side 312 can be removed to assist in reduction of lisping when the removable oral device is in place. If desired, a crescent shape (or other shape) may be provided at the anterior side 312 to reduce lisping. In some examples, trimming the posterior side 318 of the device in a crescent shape can be performed to eliminate or reduce contact with the soft palate to address individuals with heightened gag reflex. For example, a posterior volume from line 330 toward the posterior side 314 can be removed to reduce the likelihood of gagging when the removable oral device is present in the mouth. In some examples, a crescent shape (see FIG. 5) or other non-linear shape may be provided at the posterior side to reduce gagging. In other instances, the palatal element can be trimmed or cut into various shapes for purely ornamental reasons that might increase the overall aesthetic appearance of the palatal element but generally does not provide any particular function. In certain embodiments, about 1-15% of the volume from the posterior side 314 can be removed to assist in reducing the likelihood of gagging. As noted in more detail in Application No. U.S. 62/477,764, the palatal element can be produced using printing, molding, etc. from a digital scan or from an impression mold of the user's mouth. A palatal element can then be trimmed or shaped as desired to provide a desired overall volume reduction while at the same time minimizing or reducing the likelihood of lisping and/or gagging.

Figure 4:
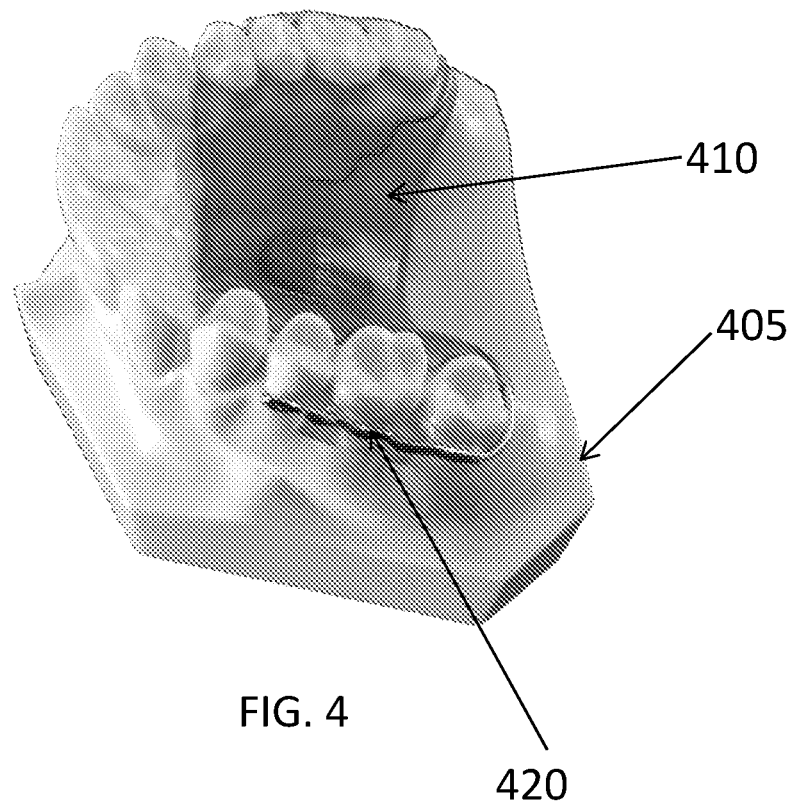
FIG. 4 is a perspective view of a removable oral device positioned within a tooth mold, in accordance with certain examples.

In certain configurations, the removable oral devices described herein may also comprise a clasping element. As noted herein, the clasping element is optional but may be present to assist removal of the palatal element from the user's mouth. Referring to FIG. 4, a perspective view of a removable oral device 400 comprising a palatal element 410 and a clasping element 420 is shown positioned around a tooth mold 405. The clasping element 420 is generally configured with a support element or wire that is embedded within a material such that the wire itself does not directly contact the outer surfaces of the teeth. While the clasping element may be configured as a wire or wires in some instances, in other cases the clasping element may comprise a plastic or flexible moldable material etc., or other non-metal based materials. In some examples, the clasping element may comprise chromium-nickel alloys such as, for example, Elgiloy materials which are cobalt-chromium-nickel alloys. In other examples, the clasping element may comprise titanium, titanium alloys, nickel titanium materials such as Nitinol, etc. In some embodiments, the material of the clasping element is generally inert so that it does not tarnish, rust, corrode or otherwise degrade during use of the removable oral device. In certain configurations, some portion of the wire may directly contact the rear surface of the back teeth to assist in retention of the palatal element 410 against the roof of a user's mouth.

Figure 5:
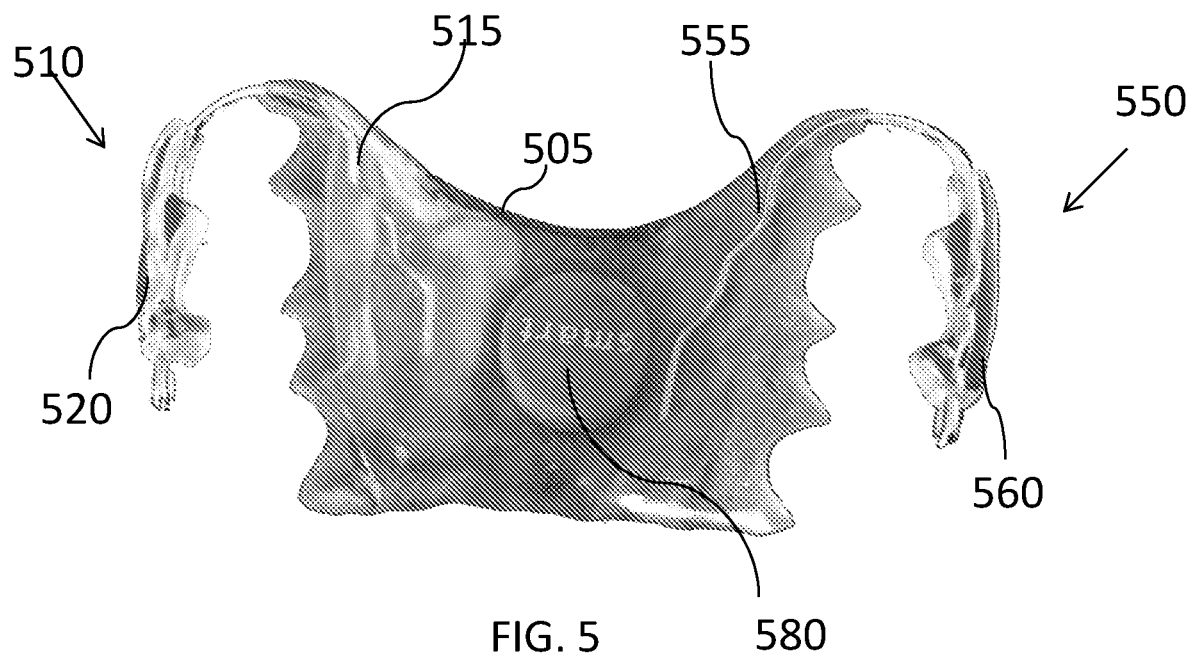
FIG. 5 is a bottom view of a removable oral device comprising a palatal element and clasping elements, in accordance with some examples.

In certain configurations, the wire of the clasping element may be a continuous wire which runs from one side of the palatal element 410 to the other or two or more separate wires can be present with one wire being present in a respective clasping element. For example and referring to FIG. 5, a clasping element 510 comprises a wire 515 and associated material 520 on some portion of the wire. Another clasping element 550 comprises a wire 555 and associated material 560 on some portion of the wire 555. Some portion of the wires 515, 555 is also embedded within a body of a palatal element 505. The material 520, 560 generally rests against outer surfaces of the teeth when the palatal element 505 is engaged to the roof of the mouth. The wires 515, 555 can assist in removal of the removable oral device from the mouth and/or assist in retaining the removable oral device in place. For example, surface tension between a palatal surface of the palatal element 505 and the roof of a user's mouth can "lock" the palatal element 505 to the roof of the mouth. The wires 515, 555 can provide leverage to assist in breaking of the surface tension and removal of the removable oral device from the mouth. An optional sensor 580 (discussed in more detail below) is also shown as being embedded in the palatal element 505. While two clasping elements 510, 550 are shown in FIG. 5, only a single clasping element may be present if desired or no clasping elements may be present at all.

In certain configurations, the palatal element and/or clasping element(s) of the removable oral devices are designed to not permanently retain the removable oral device in a user's mouth. In particular, the palatal element may lock or be held in place to the roof of the mouth without the user of any fasteners. In other examples, the clasping element can be configured to provide a friction fit against the outer surfaces of the back teeth, e.g., the clasping element is designed to contact the outer surfaces of tooth numbers 1-4 or 2-4 and/or tooth numbers 13-16 or 13-15. In some instances, the clasping element may comprise one or more portions which are positioned between two or more of tooth numbers 2-4 and/or tooth numbers 14-16 to assist in anchoring of the palatal element to the roof of the user's mouth. The removable oral device generally is designed to lack any wires, supporting element or anchoring elements which extend around, through or near tooth numbers 5-12 such that the clasping element does not alter the position of the teeth in use. As noted herein, the clasping element is also generally not designed to retain the teeth in any particular position. In some configurations, the removable oral device does not include any clasping element, supporting element, wire, etc. that engage the anterior teeth, e.g., outer surfaces of tooth numbers 5-12 or 4-11 do not contact the clasping element.

In certain embodiments, a removable oral device comprises a palatal element coupled to a clasping element. As noted herein, the palatal element is configured to contact a roof of a user's mouth at a palatal surface and can be configured to lower a vaulted area of the roof of the mouth to decrease an overall oral volume of the mouth to a first oral volume. The body of the palatal element may comprise a variable hardness across a tongue surface of the body. In some examples, the clasping element is configured to assist in removal of the removable oral device when the removable oral device is inserted into the user's mouth. In certain configurations, the tongue surface of the palatal element is compressible at an edge of the palatal element adjacent to the clasping element and is substantially non-compressible at an area adjacent to the roof of the user's mouth. For example, surfaces adjacent to the side edges, anterior edges and/or posterior edges may be soft and compressed with force from the tongue, whereas surfaces in-line with the apex surface may be substantially non-compressible by force from the tongue. It may be desirable to select materials for the edges that have a Vickers hardness soft enough to permit tongue forces to compress the material. Similarly, it may be desirable to select materials for an apex or central portion of the palatal element to have a Vickers hardness high enough such that substantially no compression of the apex or central portion occurs under tongue force or tongue pressure.

In some embodiments, the palatal element may comprise a temperature sensitive thermally expandable material configured to increase its overall volume at a body temperature of the user. For example, certain hydrogels or other gel or sol based materials may thermally expand with increasing temperature, which can act to increase the overall volume occupied by the palatal element. This configuration can result in less of a reduction in oral volume when the removable oral device is initially inserted and an increased reduction in oral volume during continued use of the removable oral device. In some examples, the thermally expandable material can be selected so that its overall volume increases by at least 5%, at least 10%, at least 15% or at least 20% when the palatal element temperature increases from around room temperature, e.g., about 25 degrees Celsius, to around body temperature, e.g., about 37 degrees Celsius. The thermally expandable material may be present, for example, in an internal bladder or compartment present in the palatal element and may or may not be accessible by the tongue during use of the removable oral device. Illustrative thermally expandable materials include, but are not limited to, thermally expandable methyacrylates, thermally expandable epoxy materials, thermally expandable hydrogels, thermally expandable aerogels and other similar materials.

Figure 6:
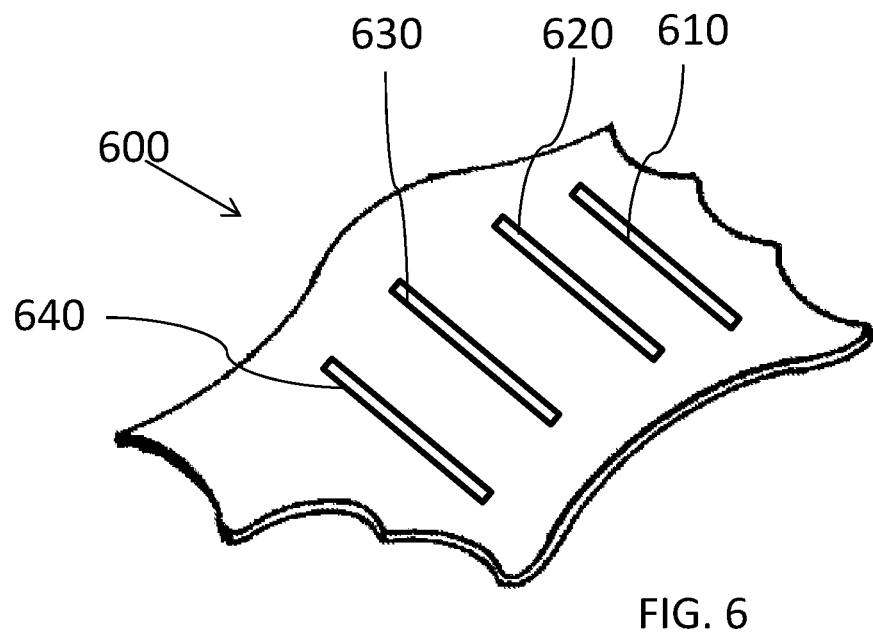
FIG. 6 is an illustration of a palatal element with grooves, in accordance with certain examples.

In certain examples, the palatal element may comprise one or more grooves, holes or other features present on a tongue surface or a palatal surface as desired. For example and referring to FIG. 6, a palatal element 600 may comprise one or more grooves such as grooves 610, 620, 630 and 640. The exact number of grooves can vary from one to about ten, for example. The grooves can assist in breaking any seal between the palatal surface and the roof of a user's mouth and/or can decrease the overall weight of the device. If desired, the grooves can be replaced with holes or other features. The grooves, holes, etc. generally do not penetrate into or through the tongue surface of the palatal element 600 to avoid materials such as food from becoming trapped in the palatal element 600. As noted herein, where grooves or other features are present, one or more sides of the palatal element 600 may also comprise soft surfaces or the palatal element may comprise a body with variable hardness.

Figure 7A:
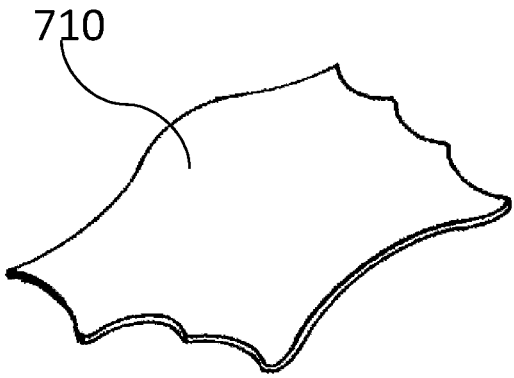
FIGS. 7A and 7B are illustrations of a stackable/couplable palatal elements in accordance with certain examples.
Figure 7B:
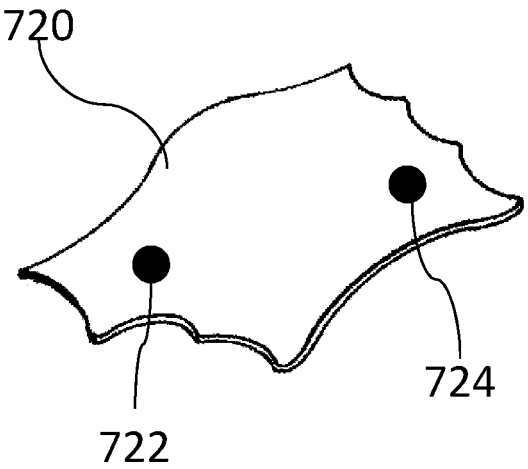

In certain configurations, the removable oral device may be modular to permit a user to assemble two or more palatal elements to each other. Referring to FIGS. 7A and 7B, two palatal elements 710, 720 are shown. A palatal surface of the element 720 may snap into or engage a tongue surface of the element 710 to retain the palatal elements 710, 720 to each other for some period. In certain configurations, the palatal element 720 may comprise projections or bosses 722, 724 which can engage corresponding holes or apertures (not shown) in an under surface of the palatal element 710 to retain the element 720 to the element 710. Coupling of the element 720 to the element 710 reduces the overall oral volume to a second oral volume which is less than that provided by either of the elements 710, 720 alone. One of the palatal elements 710, 720 may comprise one or more clasping elements as described herein to assist in retention of the assembly to the roof of the mouth of a user. If desired, a third palatal element, fourth palatal element, etc. can be coupled to further reduce the oral volume. Modular palatal elements may be particularly desirable for initial weight loss and downstream weight management. For example, both palatal elements 710, 720 can initially be used to provide a greater volume reduction and assist in weight loss from reduced caloric intake. Once the user reaches their weight goal or their BMI or body fat drops below a desired level, then one of the palatal elements 710, 720 can be removed to assist the user in maintain their current weight using only the single palatal element during ingestion of food. In the alternative, the use of multiple combined palatal elements can force a user to ingest a particular quantity of food over a desired period. For example, where a user eats food too quickly even with the removable oral device inserted, a second palatal element can be coupled to the first palatal element to provide a further reduction in oral volume to increase the overall eating time for the same quantity of food.

In certain examples, a removable oral device may comprise a palatal element, a clasping element and one or more electrical components or devices embedded or present in one or both of the palatal element and clasping element. Where the removable oral device comprising the electrical component is used in weight management/control applications, the palatal element is generally sized and arranged to reduce the overall oral volume. Where, however, the removable oral device is used in non-weight management applications, the palatal element may have a certain thickness to accommodate the electrical device or component but may not generally reduce the overall oral volume to a substantial degree. For example, where the removable oral device is used in non-weight management applications, the overall oral volume can be reduced by 20% or less or by about 15% to about 1%. In some instances, the thickness of the palatal element is sufficient to encompass or embed the electrical component within the palatal element such that the electrical component is not exposed to liquids or solids entering into the mouth.

Figure 8:
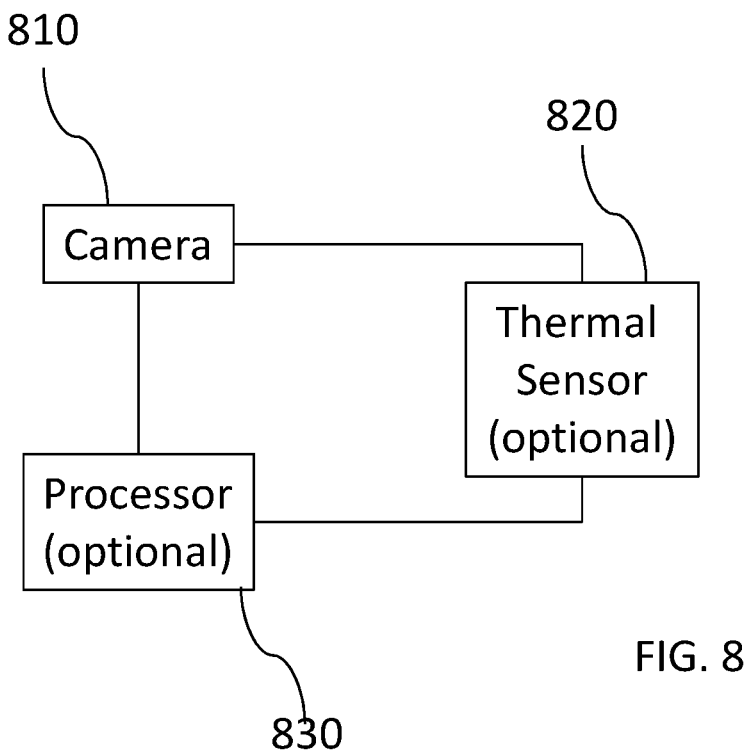
FIG. 8 is a schematic of a camera electrically coupled to a processor and which can be present in some component of a removable oral device, in accordance with certain configurations.

In certain configurations, the electrical device present in the removable oral device can be a camera embedded or present in one or both of the palatal element and clasping element. For example, a camera may be present in the palatal area to capture images, e.g., still images, video, etc., of material placed in the mouth of the user. Referring to FIG. 8, a camera 810 may comprise a rechargeable battery, e.g., one which can be charged in a wired or wireless manner, to permit the camera to operate for a selected period. The camera 810 can be electrically coupled to an optional thermal sensor 820 and a processor 830, each of which may comprise its own power source or a common power source, e.g., a battery, may be present for components 810, 820 and 830 or may be integral to one or more of these components. If desired, the processor 830 may be part of the camera 810 such that no separate processor is needed. The camera 810, optional thermal sensor 820 and optional processor 830 can all be embedded within the palatal element of the oral device such that a user cannot generally access the components 810, 820, and 830. The thermal sensor 820 can be used to sense when the device is present in the oral cavity to switch on the camera 810. The camera 810 typically comprises its own memory unit which can store the captured images. A user may transfer the images in a wired or wireless manner after the device is removed from the mouth, or the images can be transferred in real time when the device comprises an on-board transmitter/receiver as discussed in more detail below. The components 810, 820 and 830 can be integrated into a common sensor such as the sensor 580 shown in FIG. 5. If desired, an optically transparent window can be present in the palatal element to permit the camera to view the oral cavity. For example, the camera can be optically coupled to the optical window to provide for a clear view of areas underneath the optical window. The palatal element comprising the camera may comprise, if desired, a variable hardness across a tongue surface of the body, e.g., the edges may be softer than a central or apex portion of the palatal element. As noted herein, a clasping element may or may not be present in the palatal element comprising the camera. In some examples, the palatal element comprising the camera is generally not designed to retain a position of the teeth or alter a position of the teeth.

Figure 9:
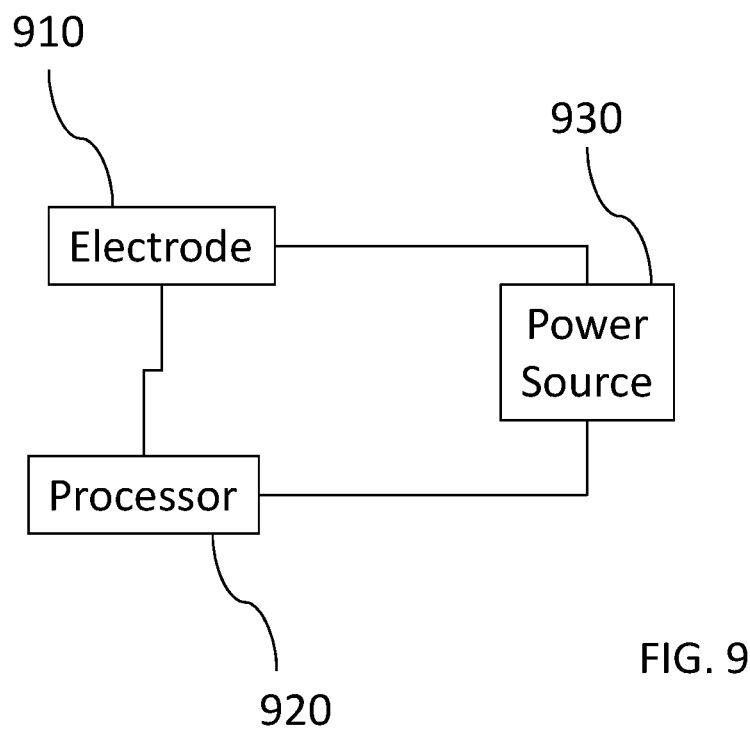
FIG. 9 is a schematic of an electrode electrically coupled to a processor and which can be present in some component of a removable oral device, in accordance with certain configurations.

In other configurations, a removable oral device may comprise a palatal element, a clasping element, and at least one electrode positioned within the body of the palatal element and exposed to fluid entering and exiting the mouth of the user. The at least one electrode can be configured, for example, to measure athletic performance from the fluid entering and exiting the mouth of the user, e.g., by comprising an exposed surface on or in the tongue surface of the palatal element. In some examples, the electrode is configured to measure the level of carbon dioxide being exhaled or inhaled by the user. In other examples, the electrode is configured to measure the level of oxygen being exhaled or inhaled by the user, e.g., can be an oxygen sensitive electrode. In some configurations, a terminal portion of the electrode at the tongue surface can be exposed to the fluid to permit electrochemical methods to be used to measure the gases or other fluids, e.g., water. For example and referring to FIG. 9, an electrode 910 can be electrically coupled to a processor 920 and a power source 930. Gases or water can contact an exposed terminal portion of the electrode 910. The electrode 910 can be configured similar to an ion selective electrode such that it is only sensitive to one or two fluids. In some examples, two or more electrodes can be present with each electrode being configured to detect a single gas or other single fluid. In some examples, the electrode may be produced from, or comprise a coating of, a polymer or a heteropolysiloxane to render the electrode sensitive to a single gas or fluid, e.g., carbon dioxide. In other examples, the electrode may comprise a catalytic platinum coating or surface to render the electrode sensitive to a single gas or fluid, e.g., oxygen. A change in measured current can be monitored and correlated to the level of gas or other fluid present during athletic activities. These measurements may be used to monitor the aerobic and/or anaerobic activity levels of an athlete during training, for example. If desired, the electrode can be used in combination with an optical sensor, e.g. infrared sensor, to further enhance monitoring of athletic performance. In some examples, the electrode may be present or part of the clasping element instead of being present in the palatal element, or a second electrode can be present in one of the palatal element and the clasping element as desired. The palatal element comprising the electrode may comprise, if desired, a variable hardness across a tongue surface of the body. As noted herein, a clasping element may or may not be present in the palatal element comprising the electrode. In certain examples, the palatal element comprising the electrode is generally not designed to retain a position of the teeth or alter a position of the teeth. In some configurations of a palatal element comprising an electrode used in non-weight management applications, the palatal element may have a certain thickness to accommodate the electrode but may not generally reduce the overall oral volume to a substantial degree. For example, where the removable oral device comprising the electrode is used in non-weight management applications, the overall oral volume can be reduced by 20% or less or by about 15% to about 1%.

Figure 10:
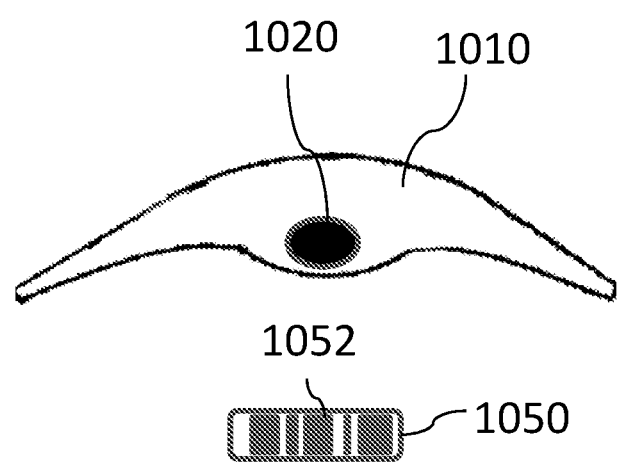
FIG. 10 is an illustration of a palatal element comprising a bar code reader, in accordance with certain configurations.
Figure 11:
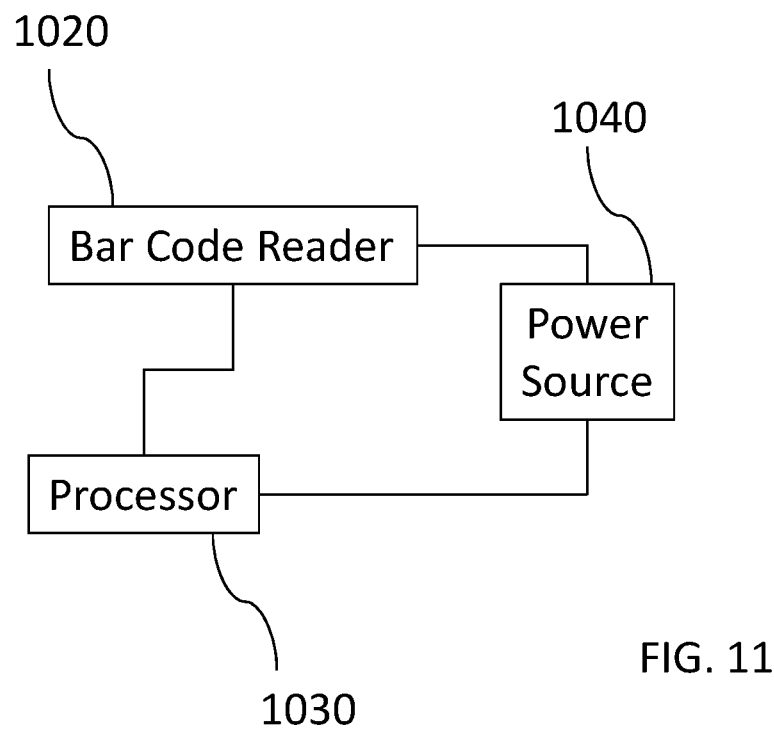
FIG. 11 is a schematic of a bar code reader electrically coupled to a processor and which can be present in some component of a removable oral device, in accordance with certain configurations.

In certain examples, a removable oral device may comprise a palatal element, a clasping element and a bar code reader. For example, the bar code reader can be present within the body of the palatal element and configured to read a bar code present on a material placed in the mouth of the user, e.g., food with a bar code, pharmacological agents with a bar code, etc. In some examples, a bar code reader 1020 can be electrically coupled to a processor 1030 and a power source 1040 as shown in FIGS. 10 and 11. The bar code reader 1020 can emit an optical signal, e.g., light, which is incident on a bar code 1052 printed or present on a material 1050 such as a tablet, capsule, food, etc. As discussed in more detail in the commonly assigned Application Nos. 62/477,760 and 62/477,766, a removable oral device with a bar code reader can be used to monitor food intake, drug intake or intake of other materials. In some instances, the bar code reader can be designed to read bar codes on opiates or other narcotics to ensure a user is actually taking the opiates or other narcotics. In some configurations, the bar code reader can be designed to measure the bar code for a selected period to permit the food or other material to dissolve to some degree and avoid a user tricking the bar code reader by placing material in the mouth and then removing the material from the mouth. For example, a pharmacological agent can be embedded or disposed in a dissolvable tape or film (or a non-dissolvable but edible tape or film) comprising the bar code. Placement of the tape in the user's mouth for a dissolving period can ensure the drug on the tape enters into the user's system to monitor drug intake compliance. The tapes may comprise, for example, polysaccharides, gelatins or other materials which are commonly used as excipients in the pharmaceutical industry. The bar code reader can be designed to use infrared light and may comprise, for example, a reader, a charged coupled device, photodiode, optical sensor or other devices which can detect light reflections. The bar code reader may also comprise one or more light sources, lenses, etc. to provide light to a surface comprising a bar code to be read. The palatal element comprising the bar code reader may comprise, if desired, a variable hardness across a tongue surface of the body e.g., the edges may be softer than an apex or central portion of the palatal element. If desired, the bar code reader can be used with a thermal sensor and/or electrode present in the body of the palatal element as described herein. As noted herein, a clasping element may or may not be present in the palatal element comprising the bar code reader. In some examples, the palatal element comprising the bar code reader is generally not designed to retain a position of the teeth or alter a position of the teeth. In certain configurations of a palatal element comprising a bar code reader used in non-weight management applications, the palatal element may have a certain thickness to accommodate the bar code reader but may not generally reduce the overall oral volume to a substantial degree. For example, where the removable oral device comprising the bar code reader is used in non-weight management applications, the overall oral volume can be reduced by 20% or less or by about 15% to about 1%.

Figure 12:
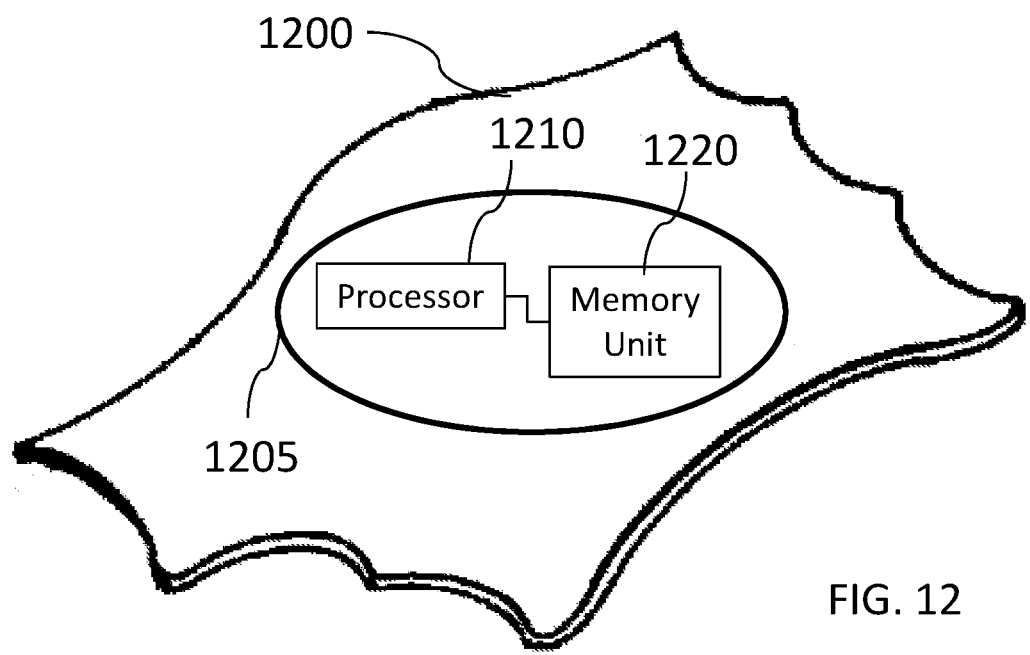
FIG. 12 is an illustration of a palatal element comprising a processor, in accordance with certain examples.
Figure 13:
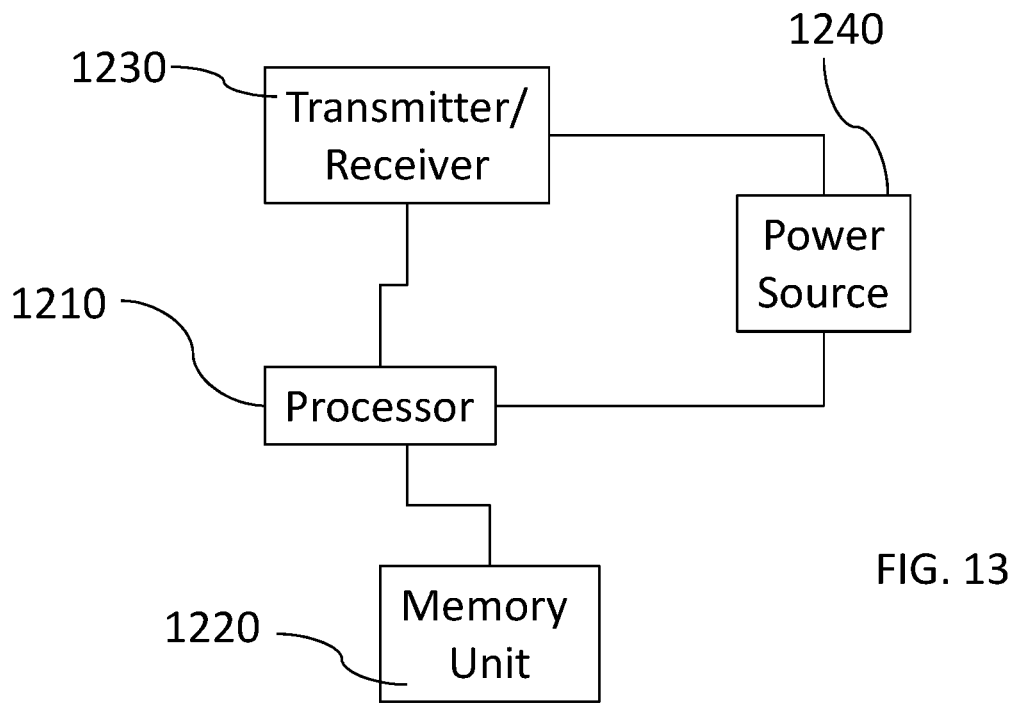
FIG. 13 is a schematic of a transmitter/receiver electrically coupled to a processor and which can be present in some component of a removable oral device, in accordance with certain configurations.

In some configurations, a removable oral device may comprise a palatal element, a clasping element, and a processor comprising a memory unit. The memory unit can be used to store many different items including, for example, storing of a user's electronic medical record or other health information. Referring to FIG. 12, a palatal element 1200 comprising a processor 1210 and a memory unit 1220 is shown. The processor 1210 and memory unit 1220 may be present in a common housing of a sensor 1205. As shown in FIG. 13, the processor 1210 and memory unit 1220 can also be used in combination with a transmitter/receiver 1230. In some examples, the transmitter/receiver 1230 is configured as a wireless transmitter/receiver or a wired transmitter/receiver. When the component 1230 is configured as a wireless transmitter/receiver, the transmitter/receiver may comprise one or more of a Bluetooth device, a cellular chip (e.g., a GSM chip, CDMA chip, etc.), a Wi-Fi device, a near field communication device, an optical transmitter or other transmitters/receivers. The processor 1210 and any other components can be electrically coupled to a power source 1240, e.g., a rechargeable battery, hand crank, fuel cell, photovoltaic cell, etc. In some examples, the rechargeable battery is configured for wireless recharging. In certain configurations of a palatal element comprising a processor used in non-weight management applications, the palatal element may have a certain thickness to accommodate the processor but may not generally reduce the overall oral volume to a substantial degree. For example, where the removable oral device comprising the processor is used in non-weight management applications, the overall oral volume can be reduced by 20% or less or by about 15% to about 1%.

In certain examples, the removable oral device may comprise a radio frequency identification tag (or other unique identifier) within the body of the palatal element. The radio frequency identification tag can be configured to pair with a sensor present in a case configured to receive the removable oral device, e.g., to store it, prior to transfer of information to or from the memory unit of the removable oral device in order to confirm the removable oral device is the proper device for that particular user. In other instances, the radio frequency identification tag can be configured to pair with one or more biometric features, e.g., a fingerprint, of the user prior to transfer of information to or from the memory unit of the removable oral device once the biometric feature is confirmed. These features permit, for example, transfer of information to/from the memory unit in a secure manner. The palatal element comprising the processor may comprise, if desired, a variable hardness across a tongue surface of the body. While not shown, the device with the transmitter/receiver may also comprise other sensors, e.g., temperature sensors, to control the on or off state of the components to preserve power, magnetic sensors to detect trace amounts of metals or other magnetic materials, etc. As noted herein, a clasping element may or may not be present in the palatal element comprising the processor. In some examples, the palatal element comprising the processor is generally not designed to retain a position of the teeth or alter a position of the teeth.

In certain examples, the removable oral device may comprise an optical transmitter within the body of the palatal element. The optical transmitter can be configured to provide optical signals to a case configured to receive the removable oral device, e.g., to store it, prior to transfer of information to or from the memory unit of the removable oral device in order to confirm the removable oral device is the proper device for that particular user. These features permit, for example, transfer of information to/from the memory unit in a secure manner. The palatal element comprising the optical transmitter may comprise, if desired, a variable hardness across a tongue surface of the body, e.g., the edges may be softer than an apex or central portion of the palatal element. While not shown, the device with the transmitter/receiver may also comprise other sensors, e.g., temperature sensors, to control the on or off state of the components to preserve power, magnetic sensors to detect trace amounts of metals or other magnetic materials, etc. As noted herein, a clasping element may or may not be present in the palatal element comprising the processor. In some examples, the palatal element comprising the processor is generally not designed to retain a position of the teeth or alter a position of the teeth.

Figure 14:
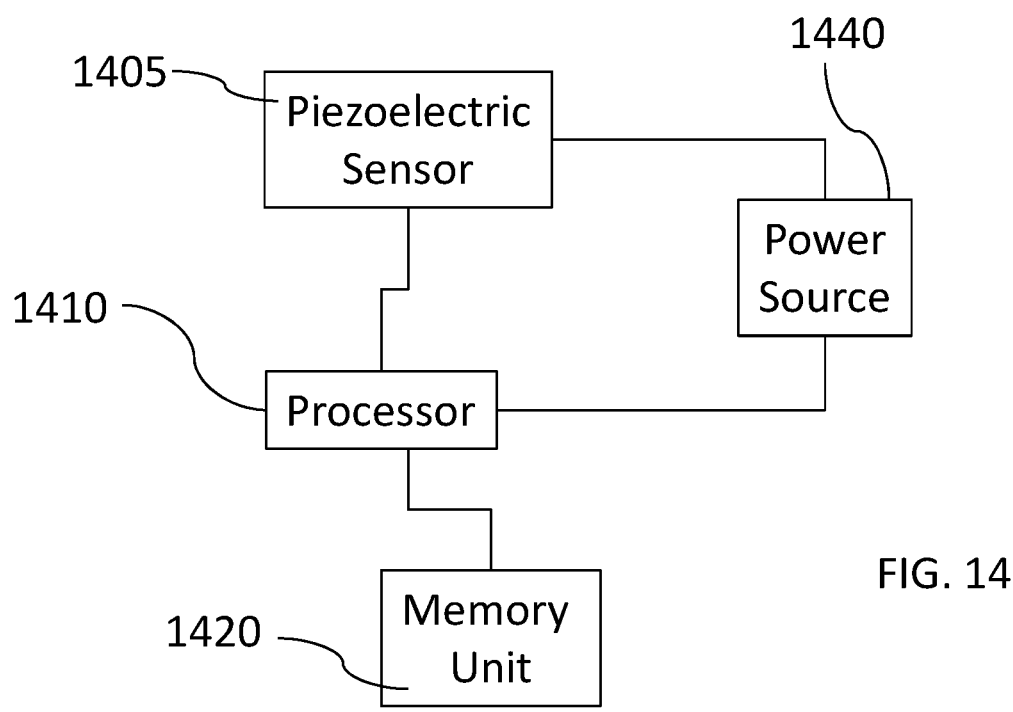
FIG. 14 is a schematic of a piezoelectric sensor electrically coupled to a processor and which can be present in some component of a removable oral device, in accordance with certain configurations.

In another configuration, a removable oral device may comprise a palatal element coupled to a clasping element and a piezoelectric sensor within the body of the palatal element. Without wishing to be bound by any particular theory, the presence of a piezoelectric sensor within the body of the palatal element permits monitoring of pressure changes, acceleration, temperature, strain, or other forces. In some examples, the piezoelectric sensor is configured to measure movement of the upper jaw to monitor chewing of food using the removable oral device. In some examples and referring to FIG. 14, a piezoelectric sensor 1405 can be electrically coupled to a processor 1410 and a power source 1440. An optional memory unit 1420 can be present in the processor 1410 or electrically coupled to the processor 1410. If desired, other components such as thermal sensors, electrodes, bar code readers, etc. can also be present. In some examples, a thermal sensor is present and used to switch on the piezoelectric sensor 1405 when the thermal sensor detects a temperature substantially the same as normal human body temperature. This switching in response to a sensed temperature can, for example, preserve battery life. In some instances, the processor 1410 is configured to switch off the piezoelectric sensor 1405 after a selected period from when the piezoelectric sensor 1405 is switched on. In other instances, the processor 1410 is configured to switch off the piezoelectric sensor 1405 when the thermal sensor detects a temperature below normal human body temperature. If desired, the piezoelectric sensor can also be used in combination with a transmitter/receiver electrically coupled to the processor. The transmitter/receiver can be configured as a wireless transmitter/receiver or a wired transmitter/receiver. Where a wireless transmitter/receiver is present, the transmitter/receiver may comprise one or more of a Bluetooth device, a cellular chip, a Wi-Fi device, a near field communication device and an optical transmitter. All of these components can be present in a common housing, for example, that is embedded within the palatal element of the removable oral device. The palatal element comprising the piezoelectric sensor may comprise, if desired, a variable hardness across a tongue surface of the body, e.g., the edges may be softer than an apex or central portion of the palatal element. As noted herein, a clasping element may or may not be present in the palatal element comprising the piezoelectric sensor. In some examples, the palatal element comprising the piezoelectric sensor is generally not designed to retain a position of the teeth or alter a position of the teeth. In certain configurations of a palatal element comprising a piezoelectric sensor used in non-weight management applications, the palatal element may have a certain thickness to accommodate the piezoelectric sensor but may not generally reduce the overall oral volume to a substantial degree. For example, where the removable oral device comprising the piezoelectric sensor is used in non-weight management applications, the overall oral volume can be reduced by 20% or less or by about 15% to about 1%.

Figure 15:
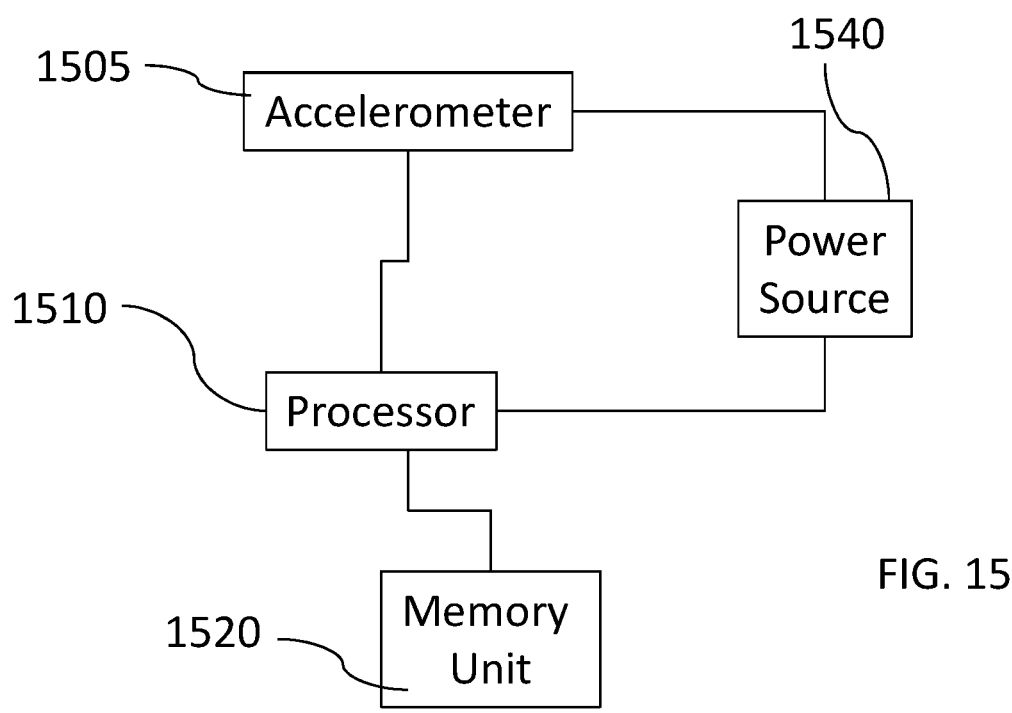
FIG. 15 is a schematic of an accelerometer electrically coupled to a processor and which can be present in some component of a removable oral device, in accordance with certain configurations.

In certain configurations, a removable oral device comprises a palatal element coupled to a clasping element, and an accelerometer within the body of the palatal element, wherein the accelerometer is configured to measure impact force. If desired, the palatal element can be coupled to, or part of, a mouthpiece designed to protect the teeth from impact. For example, players in professional football, hockey and other sports typically wear a mouthpiece to protect their teeth. A palatal element can be part of the mouthpiece, or separate from it if desired, and may include an accelerometer designed to measure the speed at which the palatal element moves from a first position to a second position. This speed can be used as a measure of impact force since head impact force generally correlates directly to velocity. Where the palatal element is present as part of a mouthpiece, the mouthpiece generally comprises a groove or tray designed to receive and protect the upper teeth, e.g., similar to an existing athletic mouthpiece, coupled to a palatal element. In some examples and referring to FIG. 15, an accelerometer 1505 can be electrically coupled to a processor 1510 and an optional memory unit 1520. A power source 1540 can be electrically coupled to the accelerometer as well. In some examples, the removable oral device comprises a thermal sensor electrically coupled to the processor, e.g., the processor is configured to switch on the accelerometer when the thermal sensor detects a temperature substantially the same as normal human body temperature. In other instances, the processor is configured to switch off the accelerometer after a selected period from when the accelerometer is switched on. In some configurations, the processor is configured to switch off the accelerometer when the thermal sensor detects a temperature below normal human body temperature. In certain examples, the removable oral device may comprise a transmitter/receiver electrically coupled to the processor, e.g., a wired or wireless transmitter/receiver. In certain embodiments, the wireless transmitter/receiver comprises one or more of a Bluetooth device, a cellular chip, a Wi-Fi device, a near field communication device and an optical transmitter.

In certain instances, a player's helmet may comprise an integrated reader which can be used with the palatal element to determine the impact force and/or speed of head movement. For example, the palatal element/mouthpiece can be removed and touched to the reader surface. If the impact force of any particular player exceeds a threshold value, then an alert can be sent to a trainer, medical personnel, etc. for example. In other instances, a receiver external to a helmet can be used to read the information from the palatal element comprising the accelerometer, e.g., a reader/receiver present on the sidelines or positioned within helmet stands commonly used on football sidelines to retain player's helmets when not in use. The palatal element comprising the accelerometer may comprise, if desired, a variable hardness across a tongue surface of the body, e.g., the edges may be softer than an apex or central portion of the palatal element. As noted herein, a clasping element may or may not be present in the palatal element comprising the accelerometer. In some examples, the palatal element comprising the accelerometer is generally not designed to retain a position of the teeth or alter a position of the teeth. In certain configurations of a palatal element comprising an accelerometer used in non-weight management applications, the palatal element may have a certain thickness to accommodate the accelerometer but may not generally reduce the overall oral volume to a substantial degree. For example, where the removable oral device comprising the accelerometer is used in non-weight management applications, the overall oral volume can be reduced by 20% or less or by about 15% to about 1%.

In certain examples, a removable oral device comprises a palatal element coupled to a clasping element, and an electrode within the body of the palatal element that is configured to measure bioelectrical impedance to determine a body fat percentage of the user. If desired, the electrode may also measure hydration levels, athletic performance parameters, etc., as noted herein. As noted in more detail in U.S. 62/477,760 and U.S. 62/477,766, measurement of bioelectrical impedance can be used to determine if the user should continue use of the removable oral device or not and/or determine removable oral device use frequency. While the exact body fat percentages may vary from user to user and based on user age, gender, etc., the removable oral device can be used until the user's measured body fat percentage drops below a desired number. Measurement of body fat percentage can be a more accurate indicator of overall health than body mass index. The electrode configuration used to measure body fat percentage can be similar to that shown in FIG. 9, for example. In some examples, the electrode is electrically coupled to a processor and a power source. The processor can be configured, for example, to detect a change in impedance to determine the body fat percentage when an external current is applied to the body of the user, e.g., at an ankle or foot of the user or at both ankles or feet of the user. In some instances, the removable oral device comprises a thermal sensor electrically coupled to the processor. In other configurations, the processor is configured to switch on the electrode when the thermal sensor detects a temperature substantially the same as normal human body temperature. In some embodiments, the processor is configured to switch off the electrode after a selected period from when the accelerometer is switched on. In additional examples, the processor is configured to switch off the electrode when the thermal sensor detects a temperature below normal human body temperature. In some instances, the removable oral device comprises a transmitter/receiver electrically coupled to the processor. In certain examples, the transmitter/receiver is configured as a wireless transmitter/receiver. In other examples, the wireless transmitter/receiver comprises one or more of a Bluetooth device, a cellular chip, a Wi-Fi device, a near field communication device and an optical transmitter. The palatal element comprising the accelerometer may comprise, if desired, a variable hardness across a tongue surface of the body e.g., the edges may be softer than an apex or central portion of the palatal element. As noted herein, a clasping element may or may not be present in the palatal element comprising the electrode. In some examples, the palatal element comprising the electrode is generally not designed to retain a position of the teeth or alter a position of the teeth.

In certain examples, a removable oral device may comprise a palatal element coupled to a clasping element, wherein the clasping element is configured to assist in removal of the removable oral device from the mouth, and wherein the clasping element does not include any supporting wires or other wire structures. For example, rigid materials (but not wires) can be present to assist in retaining the palatal element to the roof of the mouth. In some examples, nylon or nylon based materials may be present in the clasping element that is coupled to the palatal element. The nylon or nylon based materials can be used in resin form in combination with the material used to produce the palatal element to provide the removable oral device. In some examples, the nylon is used in combination with a thermoplastic material, e.g., a polyolefin thermoplastic material, to provide a clasping element. If desired, the body of the palatal element may comprise a variable hardness across a tongue surface of the body e.g., the edges may be softer than an apex or central portion of the palatal element.

In other configurations, the removable oral device comprises a palatal element coupled to a clasping element at each side of the palatal element. The clasping elements may be configured to assist in removal of the removable oral device from the mouth. Each clasping element may comprise a continuous wire structure terminating in the body of the palatal element. The continuous wire structure of each clasping element may comprise a smaller outer wire diameter at termini of the wire structure within the clasping element than an outer wire diameter within the palatal element, e.g., the wire diameter at termini can be 10%, 20%, 30%, 40% or 50% less than a wire diameter of the wire structure within the palatal element. The presence of the smaller wire outside of the teeth can provide for a more comfortable oral device. In some examples, the body of the palatal element comprises a variable hardness across a tongue surface of the body e.g., the edges may be softer than an apex or central portion of the palatal element.

In another configuration, a removable oral device comprises a palatal element and a clasping element. The palatal element may comprise a lower thickness at a front section adjacent to inner surfaces of the anterior teeth to reduce lisping compared to a thickness at an apex section of the palatal element. The exact reduction in thickness near the front section as compared to the apex section may vary from user to user. In some examples, the front section may have a thickness that is about 5%, 10%, 15%, 20%, 25%, or 30% less than a thickness at the apex section of the palatal element, where thickness is measured from top to bottom of the palatal element. If desired, the body of the palatal element may comprise a variable hardness across a tongue surface of the body e.g., the edges may be softer than an apex or central portion of the palatal element. Where a reduced thickness is present at a front section of the palatal element, the front section may comprise a softer material, e.g., similar to the side surfaces of the palatal element in certain configurations, to assist in reduction of lisping and/or provide a more comfortable removable oral device. As noted herein, the removable oral device with the thinner or softer front section is not designed or intended to move the position of the teeth or retain the position of the teeth.

In certain examples, a removable oral device may comprise a palatal element coupled to a clasping element, and a chewing sensor configured to provide sensory feedback to the user between swallowing of food in the user's mouth. For example, the chewing sensor may be designed with a timing circuit designed to measure intervals after the removable oral device is inserted into a user's mouth. The timing circuit can cause vibrations, audible noises or similar sensory feedback to provide some indicator to the user regarding food intake duration. The timing circuit may be electrically coupled to a thermal sensor as noted herein to initiate the timing. If desired, the sensory feedback can be provided at five minute intervals, ten minute intervals or other selected intervals. The sensor feedback may be switched on permanently once the device has been present in a user's mouth for some period to indicate the user should stop eating. This exact duration may vary from user to use and can be altered during use of the device as noted in more detail in the applications incorporated herein by reference. In some instances, a processor may be present and is configured to provide the sensory feedback after a selected number of chews is measured by the chewing sensor, e.g., to indicate to the user it is time to swallow the food. The chewing sensor can take numerous forms and may include a motion sensor. In some examples, the body of the palatal element comprising the chewing sensor may comprise a variable hardness across a tongue surface of the body e.g., the edges may be softer than an apex or central portion of the palatal element. A clasping element may or may not be present in the palatal element comprising the chewing sensor. In some examples, the palatal element comprising the chewing sensor is generally not designed to retain a position of the teeth or alter a position of the teeth. In some examples, the timing circuit can be configured to measure total eating time and provide the measured eating time to application software to permit a coach or user to monitor the eating habits/time of the user of the removable oral device.

In certain examples, the removable oral devices described herein may be present in a kit optionally with one or more additional components or features. For example, a kit may comprise a first removable oral device and a second removable oral device. In some instances, the first removable oral device comprises a palatal element coupled to an optional clasping element. The palatal element of the first removable oral device is configured to contact a roof of a user's mouth at a palatal surface. As described herein, the palatal element of the first removable oral device may comprise a body comprising a thickness configured to lower a vaulted area of the roof of the mouth to decrease an overall oral volume of the mouth to a first oral volume. The clasping element of the first removable oral device (when present) is configured to assist in removal of the removable oral device from the user's mouth. The second removable oral device comprises a palatal element coupled to an optional clasping element where the palatal element of the second removable oral device is configured to contact a roof of a user's mouth at a palatal surface. The palatal element of the second removable oral device comprises a body comprising a thickness configured to lower a vaulted area of the roof of the mouth to decrease an overall oral volume of the mouth to a second oral volume less than the first oral volume. The clasping element of the second removable oral device (when present) is configured to assist in removal of the removable oral device from the user's mouth. In some instances, the body of one or both of the first removable oral device and the second removable oral device comprises a variable hardness across a tongue surface of the body e.g., the edges may be softer than an apex or central portion of the palatal element. In other configurations, the palatal element of the first removable device comprises a different color than the palatal element of the second removable device to facilitate easy identification of the particular device a user desires to insert. The first removable oral device may also comprise a palatal element of a different shape to permit identification of the two different removable oral devices based on aesthetic features. If desired, the kit may also comprise a third removable oral device which can lower an overall oral volume to a third oral volume less than the second oral volume. Instructions for using the removable oral devices of the kit may also be included. Where the different removable oral devices are present in a kit, the hardness across the surface of the two removable oral devices can be the same or can be different.

In some configurations, a kit may comprise a first palatal element, a second palatal element and a clasping element configured to couple to (or be coupled to) one of the first palatal element and the second palatal element. For example, the kit may comprise a first palatal element that is configured to contact a roof of a user's mouth at a palatal surface, wherein the first palatal element comprises a body comprising a thickness configured to lower a vaulted area of the roof of the mouth to decrease an overall oral volume of the mouth to a first oral volume. The kit may also comprise a second palatal element that is configured to contact a roof of a user's mouth at a palatal surface, wherein the second palatal element comprises a body comprising a thickness configured to lower a vaulted area of the roof of the mouth to decrease an overall oral volume of the mouth to a second oral volume less than the first oral volume. By producing modular palatal elements, a user can switch out the palatal element with a different palatal element as desired. If desired, the body of one or both of the first palatal element and the second palatal element comprises a variable hardness across a tongue surface of the body. In some examples, the first palatal element comprises a different color than the second palatal element to facilitate usage of a desired palatal element by a user. Instructions for using the kit to control or monitor food intake can also be included in the kit.

In some embodiments, a kit comprises a first palatal element coupled to a clasping element and a second palatal element. The first palatal element can be configured to contact a roof of a user's mouth at a palatal surface. The first palatal element comprises a body comprising a thickness configured to lower a vaulted area of the roof of the mouth to decrease an overall oral volume of the mouth to a first oral volume. The clasping element is configured to assist in removal of the removable oral device from the user's mouth. The second palatal element can be configured to reversibly couple to the first palatal element to provide a second oral volume less than the first oral volume when the first and second palatal elements are coupled to each other. In some examples, the body of one or both of the first palatal element and the second palatal element comprises a variable hardness across a tongue surface of the body. In other examples, the first palatal element comprises a different color than the second palatal element. Instructions for using the kit to control or monitor food intake can also be included in the kit.

In certain examples, the removable oral device may be present in a kit comprising a computer program product, e.g., application software or an app, which can be embodied on a computer readable storage medium for receiving information from and/or providing information to the removable oral device. In other instances, instructions in the kit may direct a user to a particular site or provide information about downloading computer program product that can be used with the removable oral device. The computer program product typically comprises suitable code to permit a mobile device (or other electronic device or medium comprising the computer program product) to receive/send information to and from the removable oral device.

In certain embodiments, the processors, sensors, etc. described herein in connection with the removable oral devices can be present or used with a computer system. The computer system typically is separate from the removable oral device, but a processor, memory chip or other device may be integrated into some component of the removable oral device as desired. At least one processor can be electrically coupled to one or more memory units to receive input data and/or store any data. The processor may be, for example an Intel PENTIUM-type processor, Motorola PowerPC, Sun UltraSPARC, Hewlett-Packard PA-RISC processors, or any other type of processor. Various aspects of removable oral devices with an on-board processor may be implemented as specialized software. A processor can be, if desired, connected to one or more memory devices, such as a disk drive, memory, or other device for storing data. Memory is typically used for storing programs and data during use of the removable oral device. Electrical components of the oral device may be coupled by an interconnection device, which may include one or more buses (e.g., between components that are integrated within a same component) and/or a network (e.g., between components that reside on separate discrete components). The interconnection device provides for communications (e.g., signals, data, instructions) to be exchanged between components of the oral device. The processor and other components are electrically coupled to a power source, which can be on-board or external. In addition, the removable oral device may comprise one or more interfaces that connect the processor to a separate device or system such as, for example, a communication network (in addition or as an alternative to the interconnection device). Illustrative interfaces include, but are not limited to, a serial ATA interface, ISA interface, PCI interface or the like or one or more wireless interfaces, e.g., a Bluetooth device, a Wi-Fi device, a Near Field Communication device, a cellular device or other wireless protocols and/or interfaces.

In certain embodiments, the storage system of the oral device typically includes a readable and writeable nonvolatile recording medium in which data can be stored. The medium may, for example, be a solid state memory chip, solid state drive or flash memory. Typically, in operation, the processor causes data to be read from the nonvolatile recording medium into another memory that allows for faster access to the information by the processor than does the medium. This memory is typically a volatile, random access memory such as a dynamic random access memory (DRAM) or static memory (SRAM). It may be located in the storage system or in the memory system. The processor generally manipulates the data within the integrated circuit memory and then copies the data to the medium after processing is completed. A variety of mechanisms are known for managing data movement between the medium and the integrated circuit memory element and the technology is not limited thereto. The technology is also not limited to a particular memory system or storage system. In certain embodiments, the removable oral device may also include specially-programmed, special-purpose hardware, for example, an application-specific integrated circuit (ASIC) or a field programmable gate array (FPGA). Aspects of the technology may be implemented in software, hardware or firmware, or any combination thereof. The removable oral device may use or include a high-level computer programming language or specially programmed, special purpose hardware.

In certain examples, the processor and any associated sensors or components of the removable oral device may together define a computer platform for which application programs in high-level programming languages may be written. It should be understood that the technology is not limited to a particular computer system platform, processor, operating system, or network. Also, it should be apparent to those skilled in the art, given the benefit of this disclosure, that the present technology is not limited to a specific programming language or computer system. Further, it should be appreciated that other appropriate programming languages and other appropriate electrical components could also be used. In certain examples, the hardware or software can be configured to implement cognitive architecture, neural networks or other suitable implementations. In some instances, various configurations may be programmed using an object-oriented programming language, such as SmallTalk, Basic, Java, C++, Ada, or C# (C-Sharp). Other object-oriented programming languages may also be used. Alternatively, functional, scripting, and/or logical programming languages may be used. Various configurations may be implemented in a non-programmed environment (e.g., documents created in HTML, XML or other format that, when viewed in a window of a browser program, render aspects of a graphical-user interface (GUI) or perform other functions). Certain configurations may be implemented as programmed or non-programmed elements, or any combination thereof.

In certain embodiments, the removable oral device may comprise (or interact with) a mobile device, e.g., a phone or a tablet, that is configured to control use of (or monitor use of) the removable oral device. The mobile device may wirelessly communicate with the removable oral device to send signals and receive signals or data from the removable oral device. In addition, the mobile device can be pre-programmed or pre-configured to implement certain operations or applications that can automatically load from the mobile device into the removable oral device. If desired, the mobile device can be designed for use with two or more different removable oral device to permit a single mobile device to implement the same or different operations on the two or more removable oral devices. The mobile device can couple to the removable oral device in a wired or wireless manner, e.g., using near field communication, Bluetooth, or other wireless devices and protocols, to send and receive information from the mobile device to the removable oral device. One or more menus can be present on the mobile device to permit the user to select the particular methodology of using the removable oral device.

In certain configurations, the removable oral devices described herein can be used in combination with a weight management application, e.g., a software application present on a mobile device, wearable device or other electronic device, and optionally in combination with one or more coaching platforms. For example, a removable oral device can be inserted into the mouth of a user during consumption of food. Information about usage of the removal oral device during food consumption can be transferred to a weight management application/system to permit the user to track their weight goals, food intake, device usage, etc. In some examples, a coaching platform, e.g., a live coach, in-person coach, pre-recorded coaching videos, audio, text messages or digital streams or the like, can be used in combination with the removable oral device to enhance weight loss/management even further. Additional methods of using the removable oral devices are described in more detail in the commonly assigned applications incorporated by reference herein.

When introducing elements of the examples disclosed herein, the articles "a," "an," "the" and "said" are intended to mean that there are one or more of the elements. The terms "comprising," "including" and "having" are intended to be open-ended and mean that there may be additional elements other than the listed elements. It will be recognized by the person of ordinary skill in the art, given the benefit of this disclosure, that various components of the examples can be interchanged or substituted with various components in other examples.

Although certain aspects, examples and embodiments have been described above, it will be recognized by the person of ordinary skill in the art, given the benefit of this disclosure, that additions, substitutions, modifications, and alterations of the disclosed illustrative aspects, examples and embodiments are possible.

What is claimed is:

1. A removable oral device comprising a palatal element configured to contact a roof of a user's mouth at a palatal surface, the palatal element comprising a body comprising a thickness configured to lower a vaulted area of the roof of the mouth to decrease an overall oral volume of the mouth to a first oral volume, the body comprising a variable hardness across a tongue surface of the body, wherein the variable hardness comprises a Vickers hardness that gradually decreases from a central apex to outer edges of the palatal element, wherein the removable oral device is configured for insertion into the user's mouth and being retained within the mouth during consumption of food by the user to increase an overall time it takes the user to ingest a particular volume of the food to promote satiety and an overall reduction in food intake volume, wherein the palatal element comprises a first material at the central apex of the body and a second material at the outer edges of the body, wherein the second material is softer than the first material, and wherein the second material is cross-linked to the first material.

2. The removable oral device of claim 1, further comprising a clasping element coupled to the palatal element, wherein the clasping element is configured to assist in removal of the removable oral device when the removable oral device is inserted into the user's mouth.

3. The removable oral device of claim 2, further comprising a second clasping element coupled to the palatal element, wherein the clasping element is configured to engage a first respective molar surface of the user at one side of upper molars of the user and wherein the second clasping element is configured to engage a second respective molar surface of the user at an opposite side of the upper molars of the user to assist in removal of the removable oral device from the user's mouth.

4. The removable oral device of claim 3, wherein the clasping element and the second clasping element do not engage any teeth other than the molar teeth of the user.

5. The removable oral device of claim 2, wherein the palatal element and the clasping element do not alter a position of the user's teeth.

6. The removable oral device of claim 2, wherein the palatal element and the clasping element do not retain a position of the user's teeth.

7. The removable oral device of claim 1, wherein the tongue surface of the palatal element is non-compressible at an area configured to be adjacent to the roof of the user's mouth.

8. The removable oral device of claim 7, wherein the second material at the outer edges has a decreased Vickers hardness at body temperature compared to room temperature.

9. The removable oral device of claim 1, wherein the body of the palatal element is configured to reversibly couple to a second body, wherein the coupled body and second body provide a second oral volume less than the first oral volume.

10. The removable oral device of claim 9, wherein the second body is configured to reversibly couple to a third body, wherein the coupled body, second body and third body provide a third oral volume less than the second oral volume.

11. The removable oral device of claim 1, wherein a Vickers Hardness of the second material at the outer edges, when the removable oral device is inserted into the user's mouth and is at a mouth temperature of the user, is at least 20% less than a Vickers Hardness of the first material.

12. The removable oral device of claim 11, wherein the Vickers Hardness of the first material is at least 20 HV.

13. The removable oral device of claim 1, wherein the palatal element comprises a temperature sensitive thermally expandable material configured to increase its overall volume at a body temperature of the user.

14. The removable oral device of claim 1, wherein the palatal element comprises one or more longitudinal grooves.

15. The removable oral device of claim 1, wherein the palatal element comprises an internal bladder.

16. The removable oral device of claim 1, further comprising a camera embedded in the palatal element.

17. The removable oral device of claim 1, further comprising an electrode positioned within the palatal element and comprising a surface configured to be exposed to fluid entering into the user's mouth.

18. The removable oral device of claim 1, further comprising a bar code reader embedded in the palatal element.

19. The removable oral device of claim 1, further comprising a processor embedded in the palatal element.

\* \* \* \* \*